(12) United States Patent
Hoshino et al.

(10) Patent No.: US 10,085,701 B2
(45) Date of Patent: Oct. 2, 2018

(54) MEDICAL IMAGE SYSTEM AND JOINT CARTILAGE STATE SCORE DETERMINATION METHOD

(71) Applicant: Konica Minolta, Inc., Chiyoda-ku, Tokyo (JP)

(72) Inventors: Yoshihide Hoshino, Hachioji (JP); Satoshi Nishino, Sayama (JP)

(73) Assignee: KONICA MINOLTA, INC., Tokyo (JP)

( * ) Notice: Subject to any disclaimer, the term of this patent is extended or adjusted under 35 U.S.C. 154(b) by 285 days.

(21) Appl. No.: 14/908,739

(22) PCT Filed: Apr. 25, 2014

(86) PCT No.: PCT/JP2014/061660
§ 371 (c)(1),
(2) Date: Jan. 29, 2016

(87) PCT Pub. No.: WO2015/015851
PCT Pub. Date: Feb. 5, 2015

(65) Prior Publication Data
US 2016/0338659 A1    Nov. 24, 2016

(30) Foreign Application Priority Data

Jul. 30, 2013 (JP) ................................. 2013-157235
Sep. 13, 2013 (JP) ................................. 2013-189957

(51) Int. Cl.
*A61B 6/00* (2006.01)
*A61B 6/04* (2006.01)
(Continued)

(52) U.S. Cl.
CPC .............. *A61B 6/484* (2013.01); *A61B 6/032* (2013.01); *A61B 6/04* (2013.01); *A61B 6/4208* (2013.01);
(Continued)

(58) Field of Classification Search
CPC ..... A61B 6/484; A61B 6/4035; A61B 6/4208; A61B 6/4233; A61B 6/4241; A61B 6/4291
(Continued)

(56) References Cited

U.S. PATENT DOCUMENTS

| 5,542,423 A | 8/1996 | Bonutti |
| 5,812,629 A | 9/1998 | Clauser |

(Continued)

FOREIGN PATENT DOCUMENTS

| JP | 2008200359 A | 9/2008 |
| JP | 2009512524 A | 3/2009 |

(Continued)

OTHER PUBLICATIONS

A. Momose et al, "Phase Tomography by X-ray Talbot Interferometry for Biological Imaging" J. Appl. Phys. , vol. 45, (2006) p. 5254-5262.

(Continued)

*Primary Examiner* — Allen C. Ho
(74) *Attorney, Agent, or Firm* — Cantor Colburn LLP

(57) ABSTRACT

A medical image system includes an X-ray imaging device with a Talbot or Talbot-Lau interferometer, a reconstructed image generation unit, an extraction unit, a feature value calculation unit and a determination unit. The generation unit generates, among a differential phase image, an absorption image and a small-angle scattering image, at least the differential phase image based on an image signal obtained by the X-ray imaging device imaging a joint part. The extraction unit extracts a joint cartilage region based on the differential phase image. The calculation unit analyzes the joint cartilage region to calculate a feature value indicating a joint cartilage state. The determination unit compares the feature value with a predetermined reference value and (Continued)

determines, based on the comparison result, into which one of predetermined scores of multiple stages the joint cartilage state falls.

15 Claims, 20 Drawing Sheets

(51) Int. Cl.
  *A61B 6/03* (2006.01)
  *G06T 7/00* (2017.01)
  *G06T 11/00* (2006.01)

(52) U.S. Cl.
  CPC .......... *A61B 6/4233* (2013.01); *A61B 6/4241* (2013.01); *A61B 6/461* (2013.01); *A61B 6/505* (2013.01); *A61B 6/5217* (2013.01); *G06T 7/0012* (2013.01); *G06T 7/0014* (2013.01); *G06T 11/008* (2013.01); *A61B 6/0421* (2013.01); *A61B 6/4035* (2013.01); *A61B 6/4291* (2013.01); *A61B 6/463* (2013.01); *A61B 6/5235* (2013.01); *G06T 2207/10116* (2013.01); *G06T 2207/30008* (2013.01)

(58) Field of Classification Search
  USPC .................................................... 378/36, 62
  See application file for complete search history.

(56) References Cited

U.S. PATENT DOCUMENTS

| | | | | |
|---|---|---|---|---|
| 8,411,816 B2* | 4/2013 | Ohara | ............... | A61B 6/484 378/36 |
| 8,591,108 B2* | 11/2013 | Tada | ............... | A61B 6/00 378/207 |
| 8,632,247 B2* | 1/2014 | Ishii | ............... | A61B 6/00 378/207 |
| 8,755,487 B2* | 6/2014 | Kaneko | ............... | A61B 6/06 378/36 |
| 8,767,915 B2* | 7/2014 | Stutman | ............... | G01N 23/04 378/62 |
| 8,767,916 B2* | 7/2014 | Hashimoto | ............... | A61B 6/484 378/62 |
| 8,781,069 B2* | 7/2014 | Murakoshi | ............... | A61B 6/4233 378/36 |
| 8,824,629 B2* | 9/2014 | Ishii | ............... | G01N 23/04 378/62 |
| 8,989,474 B2* | 3/2015 | Kido | ............... | A61B 6/4291 382/132 |
| 8,995,614 B2* | 3/2015 | Nagatsuka | ............... | A61B 6/463 378/62 |
| 9,001,969 B2* | 4/2015 | Murakoshi | ............... | A61B 6/4233 378/70 |
| 9,025,725 B2* | 5/2015 | Kiyohara | ............... | A61B 6/06 378/197 |
| 9,025,726 B2* | 5/2015 | Ishii | ............... | A61B 6/484 378/62 |
| 9,044,154 B2* | 6/2015 | Hoshino | ............... | A61B 6/04 |
| 9,107,638 B2* | 8/2015 | Hoshino | ............... | A61B 6/484 |
| 9,329,141 B2* | 5/2016 | Stutman | ............... | G01N 23/046 |
| 9,510,799 B2* | 12/2016 | Makifuchi | ............... | A61B 6/4291 |
| 9,572,541 B2* | 2/2017 | Hoshino | ............... | A61B 6/5217 |
| 9,629,600 B2* | 4/2017 | Hoshino | ............... | A61B 6/484 |
| 9,665,950 B2* | 5/2017 | Kiyohara | ............... | G06T 11/00 |
| 9,672,949 B2* | 6/2017 | Makifuchi | ............... | G21K 1/067 |
| 9,855,018 B2* | 1/2018 | Hamano | ............... | A61B 6/566 |
| 9,870,610 B2* | 1/2018 | Makifuchi | ............... | G06T 7/0002 |
| 9,872,660 B2* | 1/2018 | Hamano | ............... | A61B 6/484 |

FOREIGN PATENT DOCUMENTS

| | | |
|---|---|---|
| JP | 2011101662 A | 5/2011 |
| JP | 2012135561 A | 7/2012 |
| WO | 2011033798 A1 | 3/2011 |
| WO | 2012128335 A1 | 9/2012 |

OTHER PUBLICATIONS

Felix Eckstein et al., "Quantitative MRI of cartilage and bone: egenerative changes in osteoarthritis", NMR in Biomedicine vol. 19, No. 7, 2006. 11, pp. 822-854.
International Search Report corresponding to Application No. PCT/JP2014/061160; dated Jul. 15, 2014, with English translation.
Junji Tanaka et al. , Cadaveric and in vivo human joint imaging based on differential phase contrast by X-ray Talbot-Lau interferometry, Z Med Phys., (2012) DOI: 10.1016.
K. Hibino et al. "Phase Shifting for nonsinusoidal waveforms with phase-shift errors", J. Opt. Soc. Am. A, vol. 12, (1995) p. 761-768.
M. Takeda et al. "Fourier-transform method of fringe-pattern analysis for computer-based topography and interferometry", J. Opt. Soc. Am, vol. 72, No. 1, (1982) p. 156.
Masabumi Nagashima et al., "Optimization of the joint and cartilage : diagnostic potential of the differential interferential contrast X-ray imaging (14th Japanese Research Society of Clinical Anatomy Meeting, Sep. 11, 2010)", Japanese Research Society of Clinical Anatomy Meeting, Feb. 2011, No. 11, p. 56-57.
Naoki Ishiguro, "The radiographic evaluation of rheumatoid arthritis: interpretation of radiographic findings in plain X-ray films", Journal of Clinical and Experimental Medicine (separate volume) The June issue, Jun. 5, 2011 (Jun. 5, 2011) , pp. 56-61.

* cited by examiner

MEDICAL IMAGE SYSTEM AND JOINT CARTILAGE STATE SCORE DETERMINATION METHOD

This is the U.S. national stage of application No. PCT/JP2014/061660, filed on Apr. 25, 2014. Priority under 35 U.S.C. § 119(a) and 35 U.S.C. § 365(b) is claimed from Japanese Application No. 2013-157235, filed Jul. 30, 2013, and from Japanese Application No. 2013-189957, filed Sep. 13, 2013, the disclosures of which are also incorporated herein by references.

TECHNICAL FIELD

The present invention relates to a medical image system and a joint cartilage state score determination method.

BACKGROUND ART

As an X-ray imaging device provided with an X-ray detector (Flat Panel Detector: FPD) in which conversion elements generating electric signals according to emitted X-rays are arranged and which reads the electric signals generated by the conversion elements as image signals, there is known, for example, an X-ray imaging device with a Talbot interferometer or Talbot-Lau interferometer provided with an X-ray source which emits X-rays to an X-ray detector, a plurality of diffraction gratings and so forth (refer to, for example, Patent Documents 1 to 3).

The Talbot interferometer or Talbot-Lau interferometer utilizes the Talbot effect of forming a grating image at constant intervals in a light traveling direction of coherent light when the light has passed through a first grating which is provided with slits arranged at predetermined intervals. The Talbot interferometer or Talbot-Lau interferometer forms moire fringes by a second grating being arranged at a position where a grating image of the first grating is formed with the grating direction of the second grating slightly inclined with respect to the direction of the first grating. When an object is arranged in front of the second grating, the moire is deformed. Hence, a reconstructed image(s) of a subject can be obtained by irradiating the subject arranged in front of or behind the first grating with coherent X-rays and performing mathematical operation on the obtained images of moire fringes (called "moire images").

It is known that at least three types of images, an X-ray absorption image, a differential phase image and a small-angle scattering image, can be generated by analyzing the moire images with a method based on the principles of the fringe scanning method (refer to, for example, Non-Patent Documents 1 and 2) or analyzing the moire images with the Fourier transform method (refer to, for example, Non-Patent Document 3), for example. It has been confirmed that a cartilage of a joint part can be depicted in, among these, the differential phase image (refer to, for example, Non-Patent Documents 4 and 5).

The inventors of this application and others have modified the X-ray imaging device with a Talbot interferometer or Talbot-Lau interferometer and succeeded in imaging a cartilage of a joint part at least in a differential phase image by taking moire images of not a joint part in a dissected state as in the above but a joint part in a living body and performing reconstruction thereon.

That is, as indicated by A1 in FIG. 9, according to the studies by the inventors of this application and others, it has been found out that a cartilage of a joint part can be imaged in a differential phase image obtained by performing reconstruction on moire images taken by an X-ray imaging device with a Talbot interferometer or Talbot-Lau interferometer. In FIG. 9, the edge of the cartilage of the joint part is imaged as a streak between two bones which constitute the joint part.

RELATED ART DOCUMENTS

Patent Documents

Patent Document 1: International Patent Application Publication No. 2011/033798
Patent Document 2: U.S. Pat. No. 5,812,629
Patent Document 3: Japanese Patent Application Publication No. 2008-200359

Non-Patent Documents

Non-Patent Document 1: K. Hibino et al, J. Opt. Soc. Am. A, Vol. 12, (1995) p. 761-768
Non-Patent Document 2: A. Momose et al, J. Appl. Phys., Vol. 45, (2006) p. 5254-5262
Non-Patent Document 3: M. Takeda et al, J. Opt. Soc. Am, Vol. 72, No. 1, (1982) p. 156
Non-Patent Document 4: Masabumi Nagashima and other seven persons, "Optimization of the joint and cartilage: diagnostic potential of the differential interferential contrast X-ray imaging ($14^{th}$ Japanese Research Society of Clinical Anatomy Meeting, Sep. 11, 2010)", Japanese Research Society of Clinical Anatomy Meeting, February 2011, No. 11, p. 56-57, [retrieved on Dec. 11, 2012], Internet <URL: http://www.jrsca.jp/contents/records/contents/PDF/11-PDF/p56.pdf>
Non-Patent Document 5: Junji Tanaka et al., Cadaveric and in vivo human joint imaging based on differential phase contrast by X-ray Talbot-Lau interferometry, Z MED PHYS., (2012) DOI:10.1016

SUMMARY OF THE INVENTION

Problems to be Solved by the Invention

By the way, it is known that destruction of a joint cartilage(s) is caused by arthritis, rheumatoid arthritis or the like. However, there has been not yet proposed any means which allows a doctor who makes diagnosis to quantitatively understand the stage of the destruction state of a joint cartilage(s).

The object of the present invention is to allow a doctor who makes diagnosis to quantitatively understand the stage of the destruction state of a joint cartilage(s).

Means for Solving the Problems

In order to achieve the above object, according to a first aspect of the present invention, a medical image system includes: an X-ray imaging device with a Talbot interferometer or Talbot-Lau interferometer; a reconstructed image generation unit which generates, among three reconstructed images of a differential phase image, an absorption image and a small-angle scattering image, at least the differential phase image based on an image signal obtained by the X-ray imaging device imaging a joint part; an extraction unit which extracts a region of a joint cartilage based on the generated differential phase image; a feature value calculation unit which analyzes the extracted region of the joint cartilage so as to calculate a feature value indicating a state of the joint cartilage; and a determination unit which compares the calculated feature value with a predetermined reference value and determines, based on a result of the comparison, into which one of predetermined scores of multiple stages the state of the joint cartilage falls.

According to a second aspect of the present invention, a joint cartilage state score determination method includes: generating, among three reconstructed images of a differential phase image, an absorption image and a small-angle scattering image, at least the differential phase image based on an image signal obtained by an X-ray imaging device with a Talbot interferometer or Talbot-Lau interferometer imaging a joint part; extracting a region of a joint cartilage based on the generated differential phase image; analyzing the extracted region of the joint cartilage so as to calculate a feature value indicating a state of the joint cartilage; and comparing the calculated feature value with a predetermined reference value and determining, based on a result of the comparison, into which one of predetermined scores of multiple stages the state of the joint cartilage falls.

Advantageous Effects of the Invention

According to the present invention, a doctor who makes diagnosis can quantitatively understand the stage of the destruction state of a joint cartilage(s).

EMBODIMENTS FOR CARRYING OUT THE INVENTION

Figure 1:
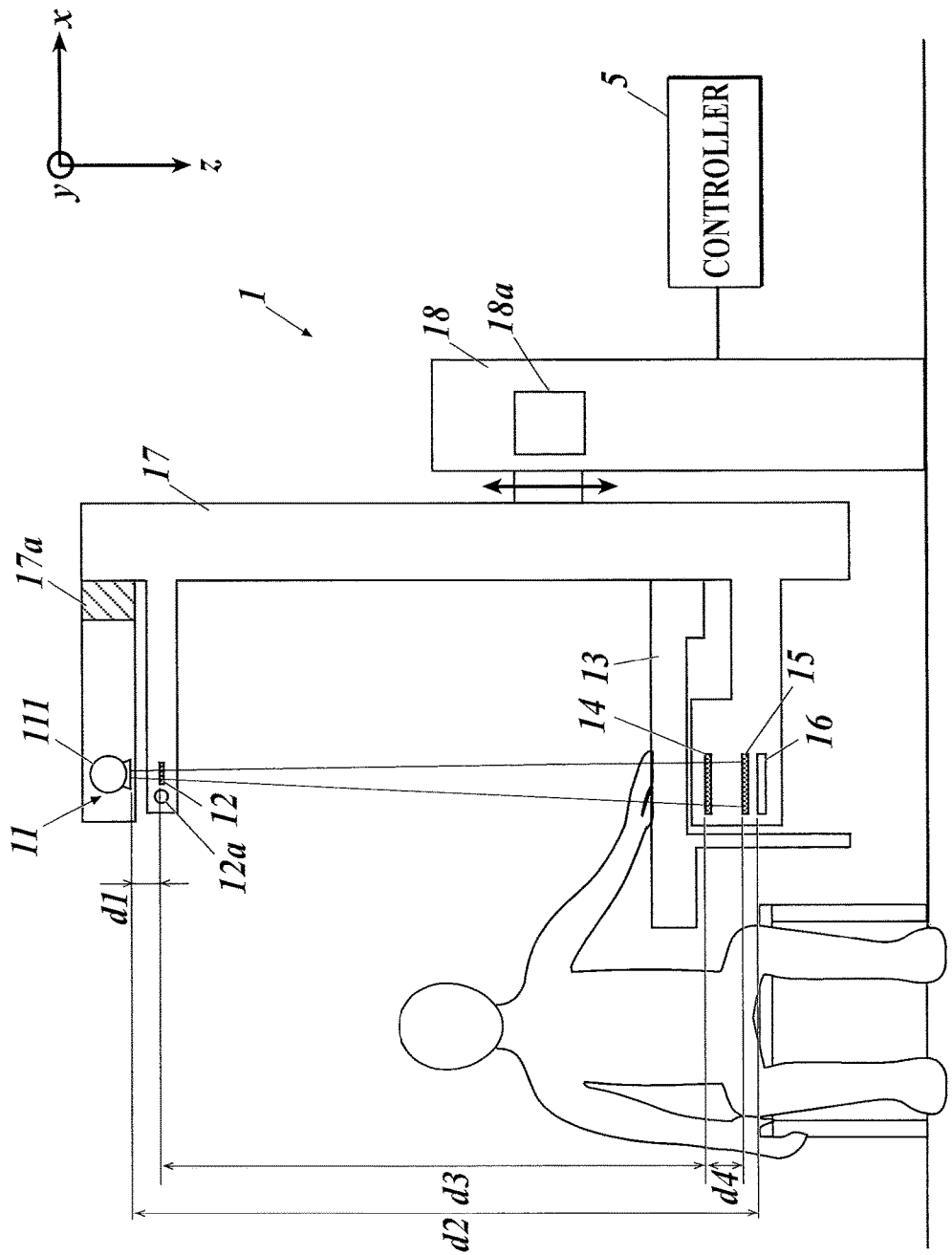
FIG. 1 shows the overall configuration of an X-ray image system according to embodiments of the present invention.

Hereinafter, embodiments of the present invention are explained, referring to the drawings.

First Embodiment

<Configuration of X-Ray Image System>

FIG. 1 shows an X-ray image system according to a first embodiment. The X-ray image system is a medical image system which includes an X-ray imaging device 1 and a controller 5. The X-ray imaging device 1 performs X-ray imaging with a Talbot-Lau interferometer, and the controller 5 generates a reconstructed image(s) of a subject using a plurality of moire images produced by the X-ray imaging.

The X-ray imaging device 1 includes, as shown in FIG. 1, an X-ray source 11, a multi-slit 12, a subject table 13, a first grating 14, a second grating 15, an X-ray detector 16, a holding unit 17 and a main body unit 18.

The X-ray imaging device 1 is a vertical type, and the X-ray source 11, the multi-slit 12, the subject table 13, the first grating 14, the second grating 15 and the X-ray detector 16 are arranged in this order in the gravity direction which is a z direction. d1 (mm) represents distance between the focal point of the X-ray source 11 and the multi-slit 12, d2 (mm) represents distance between the focal point of the X-ray source 11 and the X-ray detector 16, d3 (mm) represents distance between the multi-slit 12 and the first grating 14, and d4 (mm) represents distance between the first grating 14 and the second grating 15.

The distance d1 is preferably 5 mm to 500 mm and far preferably 5 mm to 300 mm.

The distance d2 is preferably 3,000 mm or less because the height of an X-ray room is about 3 m or less in general. The distance d2 is far preferably 400 mm to 3,000 mm and still far preferably 500 mm to 2,000 mm.

The distance (d1+d3) between the focal point of the X-ray source 11 and the first grating 14 is preferably 300 mm to 3,000 mm and far preferably 400 mm to 1,800 mm.

The distance (d1+d3+d4) between the focal point of the X-ray source 11 and the second grating 15 is preferably 400 mm to 3,000 mm and far preferably 500 mm to 2,000 mm.

As these distances, optimum distances with which a grating image (self-image) of the first grating 14 lies on the second grating 15 may be calculated and set from the wavelength of X-rays emitted from the X-ray source 11.

The X-ray source 11, the multi-slit 12, the subject table 13, the first grating 14, the second grating 15 and the X-ray detector 16 are all held by the holding unit 17, and a positional relationship thereof in the z direction is fixed. The holding unit 17 is formed in an arm shape and attached to the main body unit 18 so as to be movable in the z direction through a drive unit 18a provided in the main body unit 18.

The X-ray source 11 is held through a buffer member 17a. The buffer member 17a may be formed of any material as long as it can absorb shocks and vibrations. Examples thereof include an elastomer. The X-ray source 11 emits X-rays and thereby generates heat. Hence, the material of a part of the buffer member 17a, the part being close to the X-ray source 11, is preferably heat-insulating too.

The X-ray source (radiation source) 11 includes an X-ray tube, and generates X-rays with the X-ray tube and emits the X-rays in the gravity direction (z direction). As the X-ray tube, for example, a Coolidge X-ray tube or a rotating anode X-ray tube widely and generally used at medical sites can be used. For the anode, tungsten or molybdenum can be used.

The diameter of the focal point of the X-ray is preferably 0.03 mm to 3 mm and far preferably 0.1 mm to 1 mm.

Figure 2:
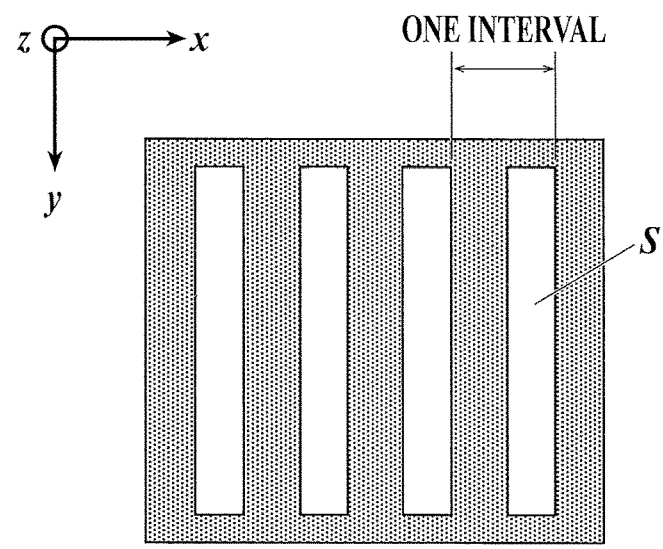
FIG. 2 is a plane view of a multi-slit.

The multi-slit (source grating) 12 is a diffraction grating in which slits S are arranged at predetermined intervals in an x direction as shown in FIG. 2. The multi-slit 12 is formed of a material having a large X-ray shielding force, namely, a material having a high X-ray absorption factor, such as tungsten, lead or gold, on a substrate made of a material having a low X-ray absorption factor, such as silicon or glass. For example, by photolithography, a resist layer is masked in the shape of slits and irradiated with UV, so that the slit pattern is transferred to the resist layer. The slit structure having the same shape as the pattern is produced by the exposure, and metal is embedded in the slit structure by electroforming Thus, the multi-slit 12 is formed.

The slit interval of the multi-slit 12 is 1 μm to 60 μm. The slit interval takes, as one interval, distance between slits S adjacent to each other as shown in FIG. 2. The slit S width (length in the x direction) is 1% to 60% of the slit interval, preferably 10% to 40% thereof. The slit S height (length in the z direction) is 1 μm to 500 μm, preferably 1 μm to 150 μm.

The slit interval of the multi-slit 12 can be obtained with the following formula, wherein $w_0$ (μm) represents the slit interval of the multi-slit 12, and $w_1$ (μm) represents the slit interval of the first grating 14.

$$w_0 = w_1 \cdot (d3+d4)/d4$$

By determining the slit interval $w_0$ in such a way as to satisfy the formula, self-images formed with the X-rays having passed through the slits S of the multi-slit 12 and the first grating 14 are superimposed on the second grating 15. This state is what is called "in focus".

As shown in FIG. 1, adjacent to the multi-slit 12, a drive unit 12a is provided. The drive unit 12a moves the multi-slit 12 in the x direction which is at right angles to the z direction. As the drive unit 12a, a drive mechanism(s) having a relatively large speed reduction ratio, such as a worm gear speed reducer, can be used alone or in combination.

The subject table 13 is where a subject is placed. In the case of the Talbot-Lau interferometer or Talbot interferometer using one-dimensional slits S like the X-ray imaging device 1, differential phase signals appear only in the slit interval direction (here, the x direction, directions slightly shifted therefrom included) of the first grating 14 and the second grating 15. Hence, for example, when a finger joint part, a knee joint part or the like is a subject region, the tip ends of joint cartilages, which are the interest region important for diagnosis, are positioned parallel to the direction (y direction) at right angles to the slit interval direction of the first grating 14 and the second grating 15 and imaged so that the differential phase signals of the tip ends of the joint cartilages can be obtained.

The first grating 14 is, as with the multi-slit 12, a diffraction grating in which slits S are arranged at predetermined intervals in the x direction (see FIG. 2). The first grating 14 can be formed by photolithography with UV as with the multi-slit 12 or may be formed by, what is called, ICP by which fine lines are deeply drilled in a silicon substrate, whereby the grating structure is formed of silicon only. The slit interval of the first grating 14 is 1 μm to 20 μm. The slit S width is 20% to 70% of the slit interval, preferably 35% to 60% thereof. The slit S height is 1 μm to 100 μm.

In the case where the first grating 14 used is a phase type, the slit S height is made to be a height with which the phase difference due to two types of materials forming the slit interval, namely, a material of an X-ray transmitting part and a material of an X-ray shielding part, becomes π/8 to 15×π/8, preferably π/4 to 3×π/8. In the case where the first grating 14 used is an absorption type, the slit S height is made to be a height with which the X-ray shielding part sufficiently absorbs X-rays.

In the case where the first grating 14 used is the phase type, the distance d4 between the first grating 14 and the second grating 15 needs to substantially satisfy the following condition.

$$d4=(m+\tfrac{1}{2})\cdot w_1^2/\lambda$$

In the above, m represents an integer, and λ represents the wavelength of X-rays.

The second grating 15 is, as with the multi-slit 12, a diffraction grating in which slits S are arranged at predetermined intervals in the x-direction (see FIG. 2). The second grating 15 can also be formed by photolithography. The slit interval of the second grating 15 is 1 μm to 20 μm. The slit S width is 30% to 70% of the slit interval, preferably 35% to 60% thereof. The slit S height is 1 μm to 100 μm.

In the embodiment, the grating planes of the first grating 14 and the second grating 15 are perpendicular to the z direction (parallel in the x-y plane). The slit S direction of the first grating 14 and the slit S direction of the second grating 15 are arranged to (slightly) incline at a predetermined angle in the x-y plane, but they may be arranged parallel.

The multi-slit 12, the first grating 14 and the second grating 15 can be configured, for example, as described below.

X-ray Source 11: Diameter of Focal Point; 300 μm, Tube Voltage; 40 kVp, Added Filter; aluminum and 1.6 mm Distance d1 from Focal Point of X-ray Source 11 to Multi-slit 12: 240 mm Distance d3 from Multi-slit 12 to First Grating 14: 1,110 mm Distance d3+d4 from Multi-slit 12 to Second Grating 15: 1,370 mm Multi-slit 12: Size; 10 mm square, Slit Interval; 22.8 μm
First Grating 14: Size; 50 mm square, Slit Interval; 4.3 μm
Second Grating 15: Size; 50 mm square, Slit Interval; 5.3 μm In the X-ray detector (radiation detector) 16, conversion elements which generate electric signals according to the emitted radiation (X-rays) are two-dimensionally arranged. The X-ray detector 16 reads the electric signals generated by the conversion elements as image signals.

The pixel size of the X-ray detector 16 is preferably 10 μm to 300 μm and far preferably 50 μm to 200 μm.

It is preferable that the X-ray detector 16 be fixed to the holding unit 17 in such a way as to contact the second grating 15. This is because, the larger the distance between the second grating 15 and the X-ray detector 16 is, the more the moire images obtained by the X-ray detector 16 are blurred.

As the X-ray detector 16, an FPD (Flat Panel Detector) can be used. There are an indirect conversion type FPD, by which detected X-rays are converted into electric signals through photo-electric conversion elements, and a direct conversion type FPD, by which detected X-rays are directly converted into electric signals. Either of them can be used.

The indirect conversion type is configured such that, under a scintillator plate made of CsI, $Gd_2O_2$ or the like, photo-electric conversion elements associating with TFTs (Thin Film Transistors) are two-dimensionally arranged, thereby constituting pixels. When absorbing the X-rays entering the X-ray detector 16, the scintillator plate emits light. This emitted light is accumulated in the photo-electric conversion elements as electric charges. The accumulated electric charges are read out as image signals.

The direct conversion type is configured such that an amorphous selenium film, having a film thickness of 100 μm to 1,000 μm, is formed on glass by thermal deposition of amorphous selenium, and the amorphous selenium film and electrodes are vapor-deposited on an array of TFTs which are two-dimensionally arranged. When the amorphous selenium film absorbs X-rays, voltage is released into the substance in the form of electron-hole pairs, and the TFTs read out voltage signals between the electrodes.

As the X-ray detector 16, an imager such as a CCD (Charge Coupled Device) or an X-ray camera may be used.

Figure 3:
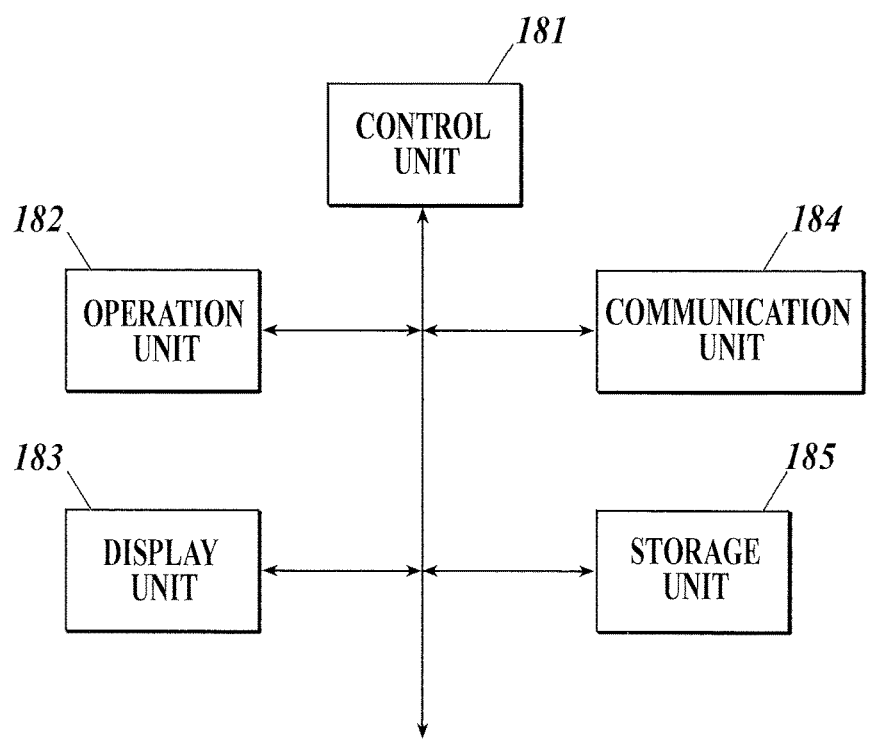
FIG. 3 is a block diagram showing the functional configuration of a main body unit shown in FIG. 1.

The main body unit 18 includes, as shown in FIG. 3, a control unit 181, an operation unit 182, a display unit 183, a communication unit 184 and a storage unit 185.

The control unit 181 includes a CPU (Central Processing Unit) and a RAM (Random Access Memory) and performs various processes by working together with programs stored in the storage unit 185. The control unit 181 is connected with the units such as the X-ray source 11, the drive unit 12a, the drive unit 18a and the X-ray detector 16 and controls, for example, timing of and conditions for emitting X-rays from the X-ray source 11, timing of reading image signals with the X-ray detector 16 and movement of the multi-slit 12 according to setting information on an imaging condition input from the controller 5.

The operation unit 182 includes an exposure switch, and generates operation signals according to the operation thereon and outputs the operation signals to the control unit 181.

The display unit 183 displays, on its display, operation screens, action statuses of the X-ray imaging device 1 and so forth under display control of the control unit 181.

The communication unit 184 includes a communication interface and communicates with the controller 5 on a network. For example, the communication unit 184 sends moire images to the controller 5, the moire images being read by the X-ray detector 16 and stored in the storage unit 185.

The storage unit 185 stores therein the programs which are executed by the control unit 181, data necessary for execution of the programs and so forth. The storage unit 185 also stores therein the moire images obtained by the X-ray detector 16.

The controller 5 controls imaging action of the X-ray imaging device 1 according to the operation by an operator. Further, the controller 5 as a medical image processing device generates a diagnostic reconstructed image(s) (of a subject), using a plurality of moire images obtained by the X-ray imaging device 1, and also analyzes the reconstructed image and displays the result.

Figure 4:
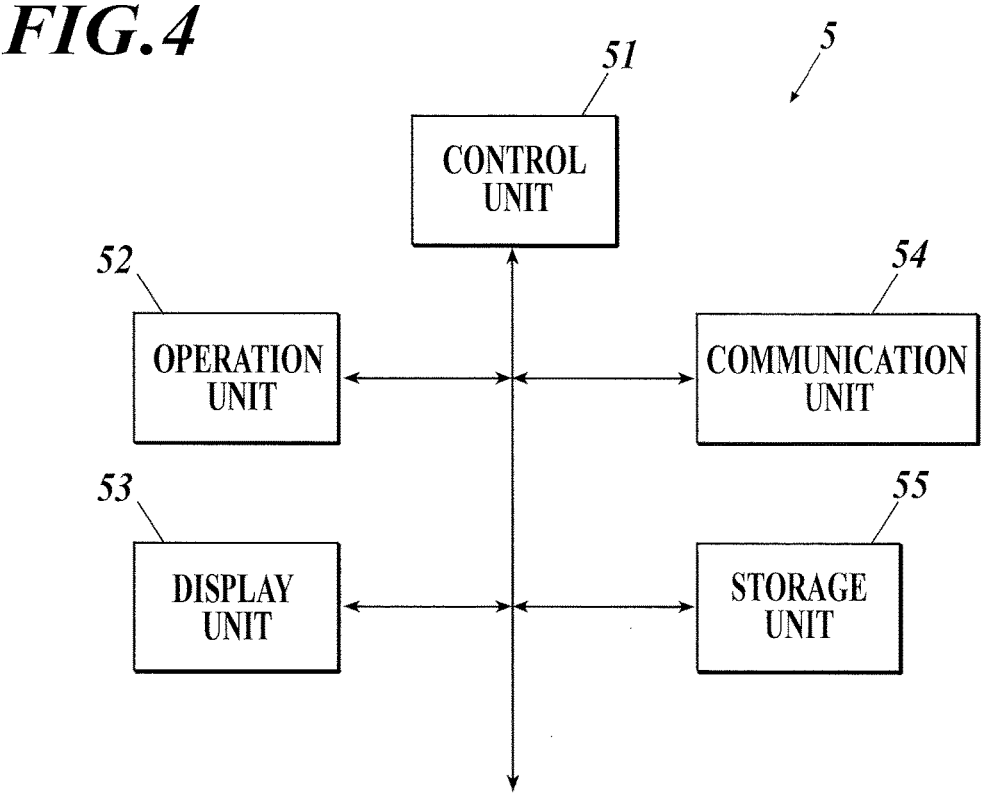
FIG. 4 is a block diagram showing the functional configuration of a controller shown in FIG. 1.

The controller 5 includes, as shown in FIG. 4, a control unit 51, an operation unit 52, a display unit 53, a communication unit 54 and a storage unit 55.

The control unit 51 includes a CPU (Central Processing Unit) and a RAM (Random Access Memory) and performs various processes including the below-described reconstructed image generation process and score determination process by working together with programs stored in the storage unit 55. The control unit 51 functions as a reconstructed image generation unit, an extraction unit, a feature value calculation unit and a determination unit.

The operation unit 52 includes: a keyboard provided with cursor keys, number input keys, various function keys and so forth; and a pointing device such as a mouse, and outputs press signals of pressed keys of the keyboard and operation signals of the mouse to the control unit 51 as input signals. The operation unit 52 may also include a touch panel integrated into a display of the display unit 53, and generate operation signals according to the operation thereon and output the signals to the control unit 51.

The display unit 53 includes a monitor such as a CRT (Cathode Ray tube) or an LCD (Liquid Crystal Display) and displays operation screens, action statuses of the X-ray imaging device 1, the generated diagnostic reconstructed images and so forth under display control of the control unit 51.

The communication unit 54 includes a communication interface and communicates with the X-ray imaging device 1 or the X-ray detector 16 on a network with or without a cable. For example, the communication unit 54 sends imaging conditions and control signals to the X-ray imaging device 1 and receives moire images from the X-ray imaging device 1 or the X-ray detector 16.

The storage unit 55 stores therein the programs which are executed by the control unit 51, data necessary for execution of the programs and so forth. For example, the storage unit 55 stores therein imaging order information which is information on imaging booked by a not-shown RIS (Radiology Information System), HIS (Hospital Information System) or the like. The imaging order information is information containing a patient ID, a patient name, an imaging region (subject region) and so forth.

The storage unit 55 also stores therein an imaging condition table in which subject regions and imaging conditions suitable for the respective subject regions are correlated with each other.

The storage unit 55 also stores therein moire images obtained by the X-ray imaging device 1 based on imaging order information and a diagnostic reconstructed image(s) generated based on the moire images being correlated with the imaging order information.

Further, the storage unit 55 stores therein gain correction data for the X-ray detector 16, a defect pixel map and so forth in advance. The defect pixel map is positional information (coordinates) of defect pixels (missing pixels included) of the X-ray detector 16.

<Action of X-ray Image System>

Hereinafter, an X-ray imaging method used by the Talbot-Lau interferometer of the X-ray imaging device 1 is explained.

Figure 5:
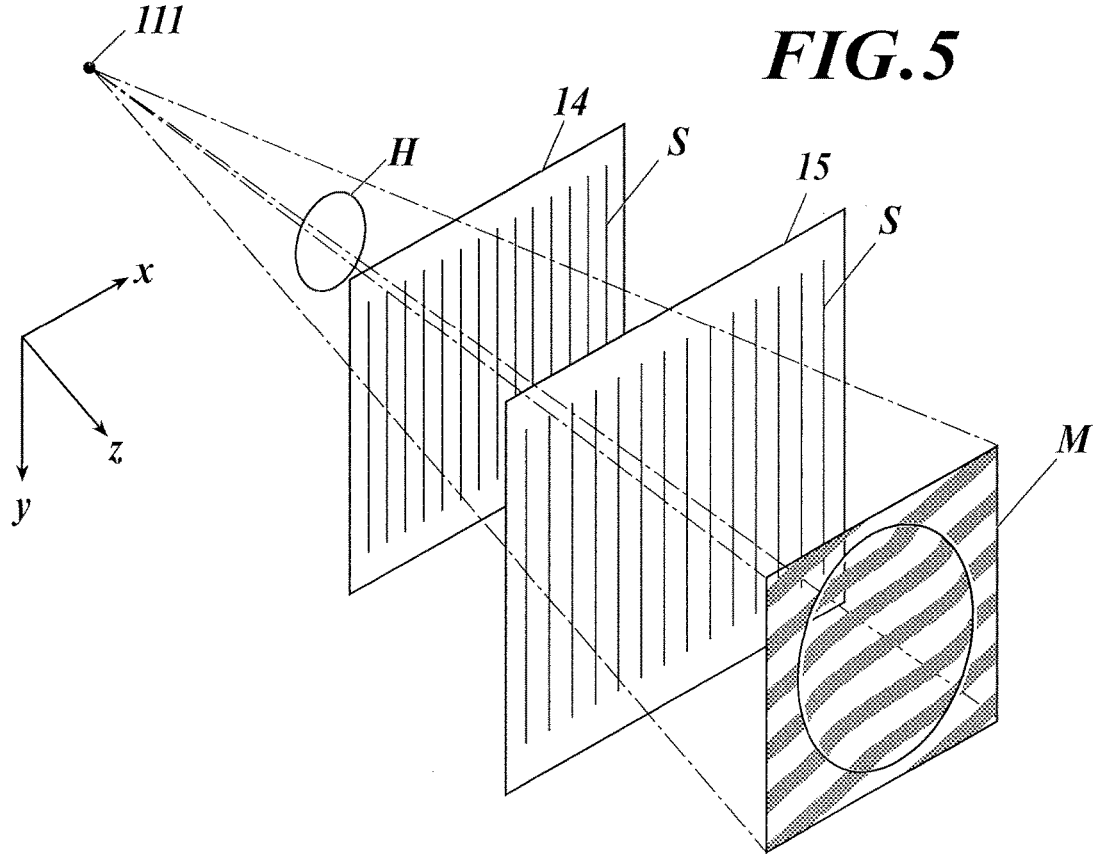
FIG. 5 is an illustration to explain principles of a Talbot interferometer.

As shown in FIG. 5, when the X-rays emitted from the X-ray source 11 has passed through the first grating 14, the X-rays having passed through the first grating 14 form an image at constant intervals in the z-direction. These images are called self-images, and phenomenon of self-images being formed is called the Talbot effect. The second grating 15 is arranged at a position where a self-image is formed, in such a way as to be approximately parallel to the self-image, and the X-rays having passed through the second grating 15 form a moire image ("M" in FIG. 5). When a subject ("H" in FIG. 5) exists between the X-ray source 11 and the first grating 14, the phase of the X-rays is shifted by the subject, so that, as shown in FIG. 5, the moire fringes on the moire image are deformed with the periphery of the subject as a border. This deformation of the moire fringes is detected by processing the moire image, so that an image of the subject is formed. This is the principles of Talbot interferometers.

In the X-ray imaging device 1, the multi-slit 12 is arranged near the X-ray source 11 between the X-ray source 11 and the first grating 14, and X-ray imaging with the Talbot-Lau interferometer is performed. The Talbot interferometer is premised on the X-ray source 11 being an ideal point source. However, in the actual imaging, a focal point of a large diameter to some extent is used. Then, through the multi-slit 12, it acts like a plurality of point sources arranged in a serial row emitting X-rays. This is the X-ray imaging method with a Talbot-Lau interferometer, which demonstrates the same Talbot effect as a Talbot interferometer demonstrates, even when the diameter of the focal point is large to some extent.

In the X-ray image system of the embodiment, the controller 5 performs the reconstructed image generation process according to the operation on the operation unit 52, whereby an imaging condition is set in the X-ray imaging device 1, and X-ray imaging is performed. The moire images produced by the X-ray imaging are sent to the controller 5, and a reconstructed image(s) are generated based on the moire images.

<Reconstructed Image Generation Process>

Figure 6:
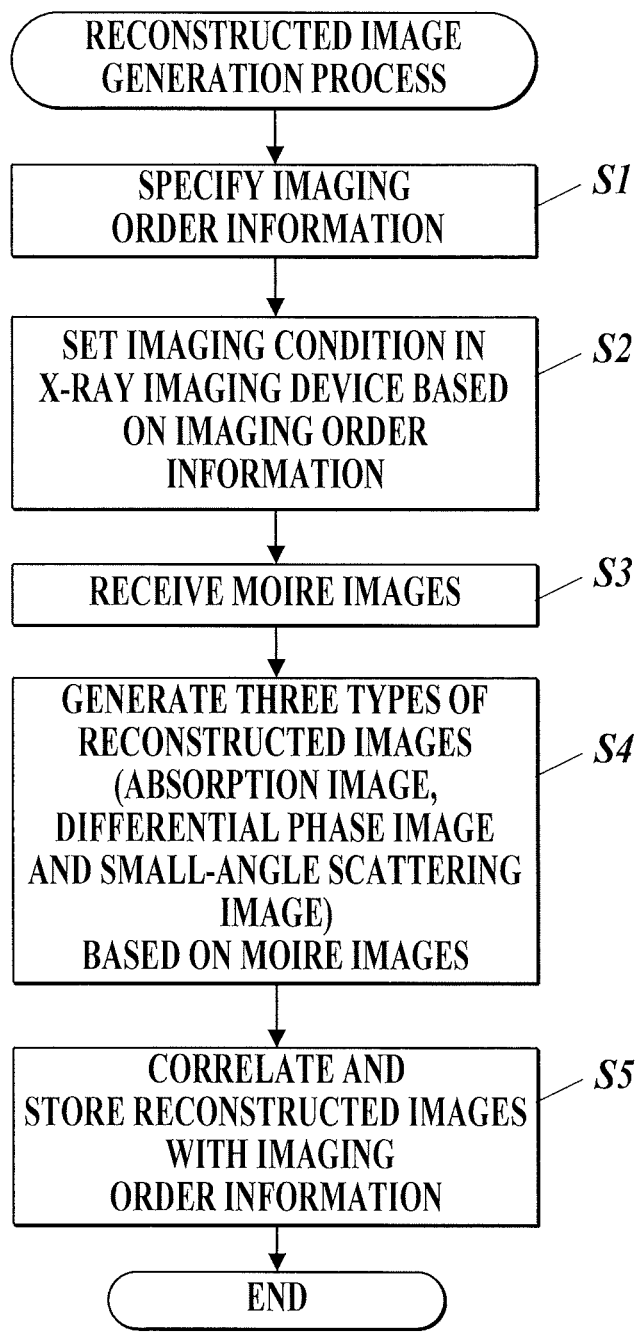
FIG. 6 is a flowchart of a reconstructed image generation process performed by a control unit shown in FIG. 4.

FIG. 6 shows a flowchart of the reconstructed image generation process performed by the control unit 51 of the controller 5. The reconstructed image generation process is performed by the control unit 51 working together with the program(s) stored in the storage unit 55 according to the operation on the operation unit 52.

First, a list of imaging order information is displayed on the display unit 53 of the controller 5, and imaging order information on an imaging target is specified through the operation unit 52 (Step S1).

Next, an imaging condition for the subject region contained in the specified imaging order information is read from the imaging condition table in the storage unit 55, and sent to the X-ray imaging device 1 through the communication unit 54 and set therein (Step S2).

When receiving the imaging condition from the controller 5, the X-ray imaging device 1 performs a series of imaging to obtain moire images necessary to generate one reconstructed image.

In a series of imaging, first, the X-ray source 11 starts emitting X-rays in a state in which the multi-slit 12 stops. In the X-ray detector 16, after resetting is performed to remove unnecessary electric charges which have remained since the last imaging, electric charges are accumulated in response to the timing of the X-ray emission, and the accumulated electric charges are read as image signals in response to the timing of the stop of the X-ray emission. This is imaging of one step. At the timing when imaging of one step ends, the multi-slit 12 starts moving. The multi-slit 12 stops moving when having moved a predetermined amount, and imaging of the next step is performed. Thus, the multi-slit 12 alternates moving with stopping a predetermined number of steps. When the multi-slit 12 stops, X-rays are emitted and image signals are read. When imaging with the multi-slit 12 having moved one interval of the slit interval ends, the series of imaging to obtain a plurality of moire images necessary to generate one reconstructed image ends accordingly. The read image signals are output to the main body unit 18 as moire images and sent to the controller 5 through the communication unit 184.

Note that X-ray imaging with a subject placed on the subject table 13 (subject-existing X-ray imaging) and X-ray imaging with no subject placed on the subject table 13 (no-subject-existing X-ray imaging) are performed.

The number of steps in the series of imaging is preferably 2 to 20 and far preferably 3 to 10. In terms of obtaining a reconstructed image with high visibility in a short period of time, five steps are preferable (Reference Document 1: K. Hibino, B. F. Oreb and D. I. Farrant, Phase shifting for nonsinusoidal wave forms with phase-shift errors, J. Opt. Soc. Am. A, Vol. 12, 761-768 (1995), and Reference Document 2: A. Momose, W. Yashiro, Y. Takeda, Y. Suzuki and T. Hattori, Phase Tomography by X-ray Talbot Interferometry for biological imaging, Jpn. J. Appl. Phys., Vol. 45, 5254-5262 (2006)). Here, imaging of five steps is performed.

Figure 7:
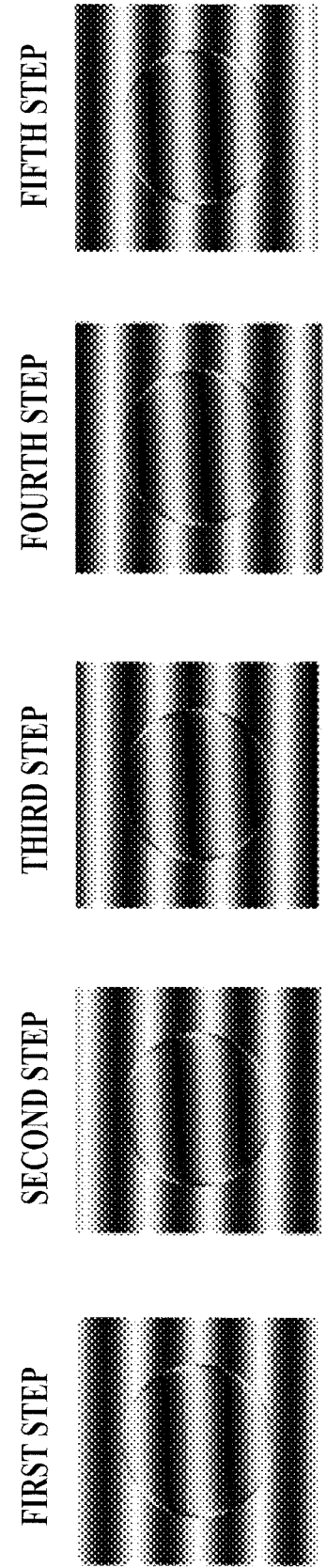
FIG. 7 shows moire images produced by imaging of five steps.

Suppose, for example, the slit interval of the multi-slit 12 is 22.8 µm, and imaging of five steps takes ten seconds, each time the multi-slit 12 moves 4.56 µm, which is ⅕ of the slit interval, and stops, imaging is performed. After the exposure switch is turned on, imaging is performed in two seconds, four seconds, six seconds, eight seconds and ten seconds in terms of imaging time. When the multi-slit 12 is movable at a constant delivery amount owing to ideal delivery accuracy, as shown in FIG. 7, imaging of five steps produces five moire images for one interval of the slit interval of the multi-slit 12.

When the moire images are received from the X-ray imaging device 1 through the communication unit 54 (Step S3), three types of diagnostic reconstructed images of a subject, an absorption image, a differential phase image and a small-angle scattering image, are generated based on the received moire images (Step S4).

The absorption image (X-ray absorption image) is generated by imaging the average component of interference fringes and has contrast according to the X-ray attenuation amount generated by a subject. The absorption image has been used for diagnosis, and hence a person in the medical profession such as a doctor is familiar therewith. The absorption image is advantageous to depiction of bones which can readily have X-ray absorption contrast.

The differential phase image is generated by imaging phase information on the interference fringes and has contrast according to the tilt amount of the X-ray wavefront generated by a subject. The differential phase image is superior in depiction of soft tissue to the absorption image.

The small-angle scattering image is generated by imaging visibility of the interference fringes and has contrast according to the X-ray scattering caused by a subject (Reference Document 3: Distribution of unresolvable anisotropic microstructures revealed in visibility-contrast images using x-ray Talbot interferometry Wataru Yashiro et. al. PHYSICAL REVIEW B 84, 094106 (2011)). The small-angle scattering image is superior in depiction of microstructures to the absorption image.

The absorption image, the differential phase image and the small-angle scattering image generated at Step S4 are generated based on the same (group of) moire images sent from the X-ray imaging device 1. Hence, the three reconstructed images depict the same part of the same subject, and alignment of the subjects of the images is unnecessary.

The above three types of reconstructed images can be generated by a well-known method described, for example, in International Patent Application Publication No. 2012/029340.

First, moire images with a subject and moire images with no subject are subjected to, for example, offset correction, gain correction, defective pixel correction and/or X-ray intensity variation correction. Next, based on the corrected moire images with the subject, three types of reconstructed images (an absorption image, a differential phase image and a small-angle scattering image) with the subject are generated. In addition, based on the corrected moire images with no subject, three types of reconstructed images (an absorption image, a differential phase image and a small-angle scattering image) with no subject are generated.

More specifically, the absorption image is generated by adding up interference fringes of a plurality of moire images, the differential phase image is generated by calculating the phase of the interference fringes with the principles of the fringe scanning method, and the small-angle scattering image is generated by calculating visibility (visibility=amplitude/average value) of the interference fringes with the principles of the fringe scanning method.

The generated reconstructed images with the subject are subjected to corrections to remove the phase of the interference fringes and to remove image unevenness, using the reconstructed images with no subject of the same types (e.g. for the small-angle scattering image with the subject, the small-angle scattering image with no subject is used), whereby three types of diagnostic reconstructed images of the final version are generated.

When generation of the diagnostic reconstructed images ends, the imaging order information specified at Step S1 is correlated and stored with the generated moire images and reconstructed images in the storage unit 55 (Step S5). Then, the reconstructed image generation process ends.

<Score Determination Process>

The controller 5 performs the score determination process to determine the state of a joint cartilage by score by analyzing a reconstructed image(s) having a joint part as a subject.

Figure 8:
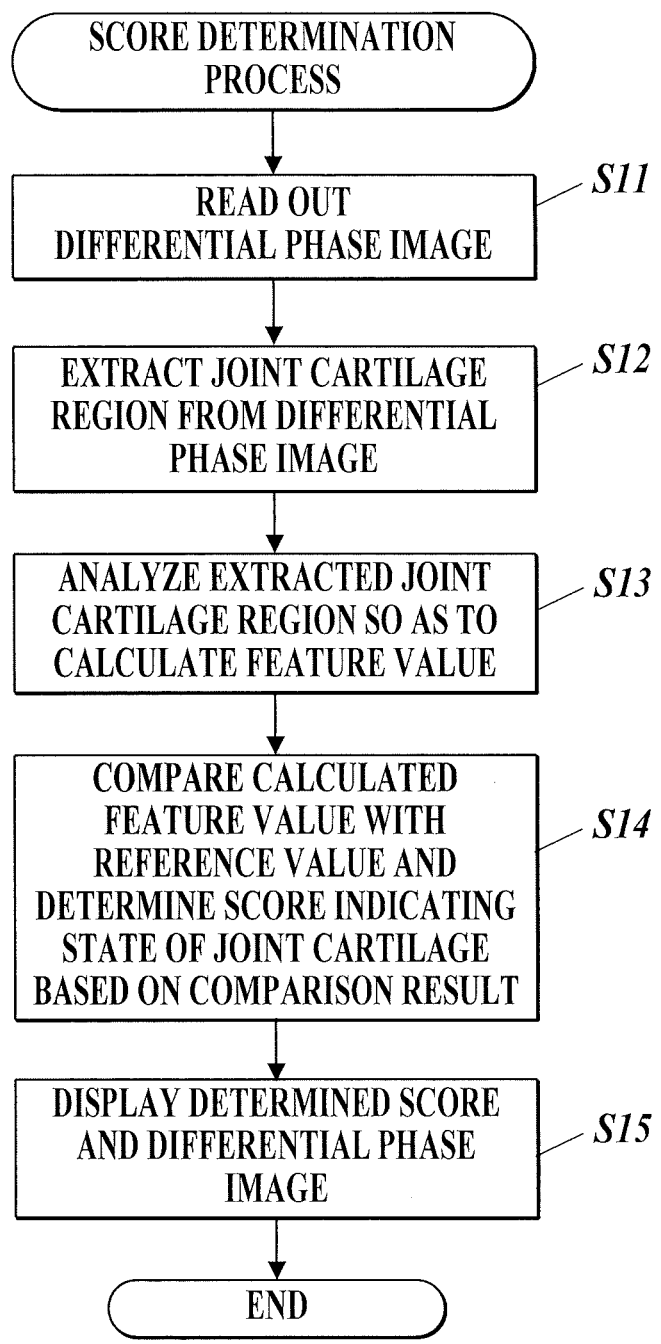
FIG. 8 is a flowchart of a score determination process performed by the control unit shown in FIG. 4.

FIG. 8 shows a flowchart of the score determination process performed by the control unit 51 of the controller 5. The score determination process is performed by the control unit 51 working together with the program(s) stored in the storage unit 55 when imaging order information correlated with a reconstructed image(s) and having a finger joint part, a knee joint part or the like as a subject region is selected and score determination is instructed through the operation unit 52.

In the score determination process, first, a differential phase image correlated with the imaging order information selected through the operation unit 52 is read from the storage unit 55 (Step S11).

Next, a joint cartilage region is extracted from the differential phase image (Step S12).

As described above, in the Talbot-Lau interferometer or Talbot interferometer using one-dimensional slits S like the X-ray imaging device 1, differential phase signals appear in the slit interval direction (here, the x direction) of the first grating 14 and the second grating 15. Hence, at Step S12, first, a profile of each line (each line extending in the x direction) of the differential phase image in the x direction is created.

Figure 9:
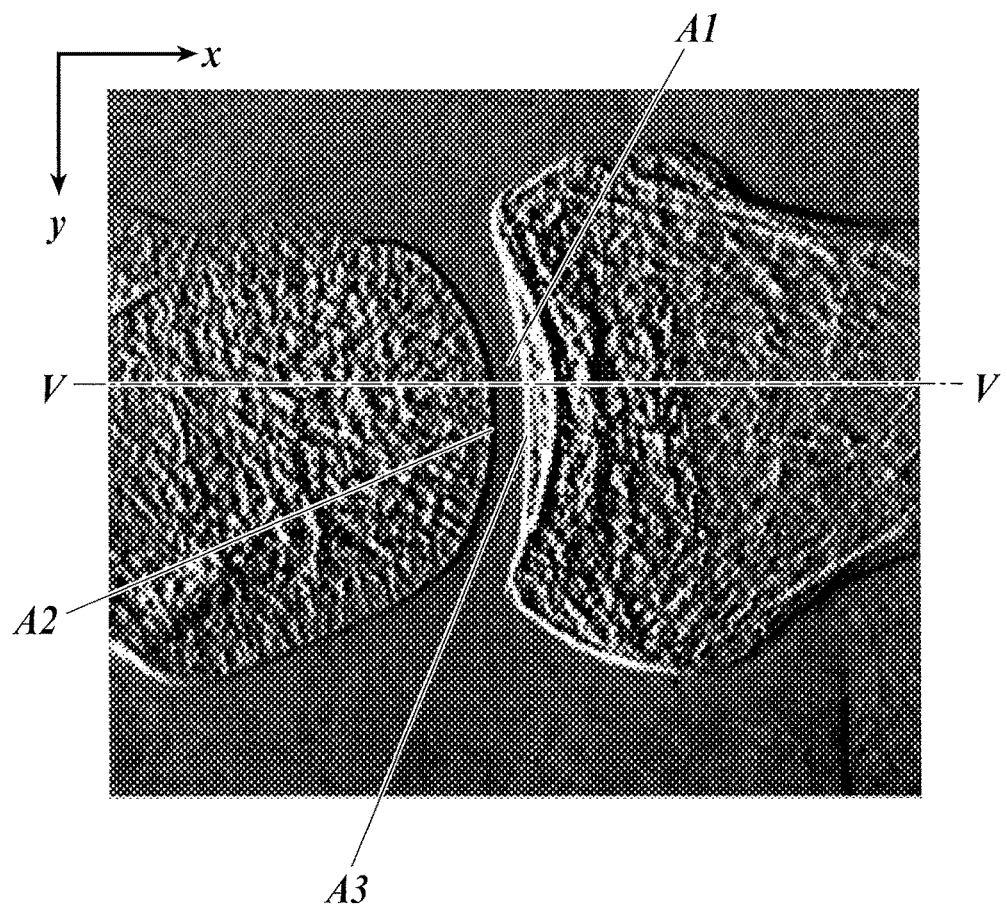
FIG. 9 shows an example of a differential phase image having a finger joint part as a subject region.

FIG. 9 shows an example of a differential phase image having a finger joint part as a subject region. In FIG. 9, the part indicated by A1 is the tip end of a joint cartilage (cartilage tip end), and the part indicated by A2 is the tip end of a bone (bone tip end) for the joint cartilage.

Figure 10:
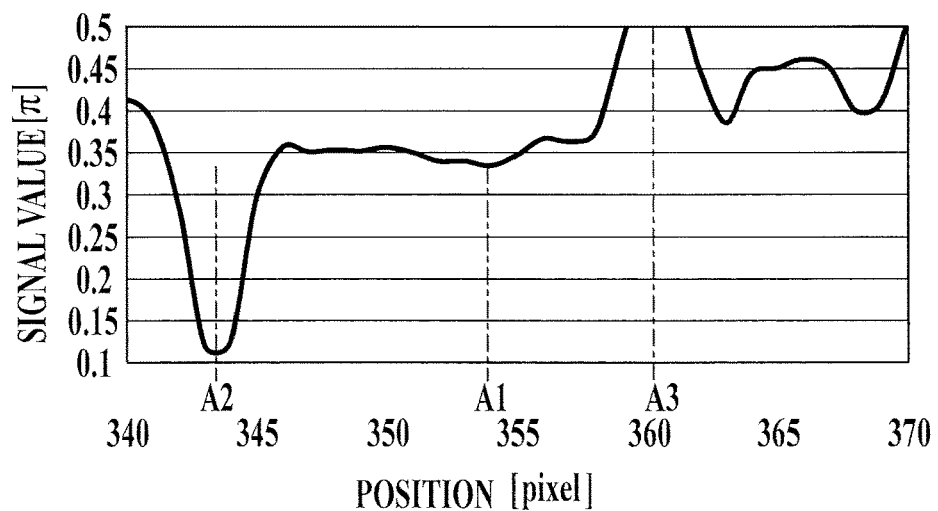
FIG. 10 shows a part of a profile in the x direction around the V-V position (a profile in the x direction around the center) in FIG. 9.

FIG. 10 shows a part of the profile in the x direction around the V-V position (the profile in the x direction around the center) in FIG. 9. In FIG. 10, the transverse axis represents a pixel position(s) in the x direction, and the vertical axis represents a signal value(s) (signal value(s) of the differential phase image).

The part (A2) having the lowest signal value in FIG. 10 is the signal of the bone tip end A2 in FIG. 9. The part (A3) having the highest signal value in FIG. 10 is the signal of the tip end A3 of the other bone in FIG. 9. The part (A1) being a local minimum value between A2 and A3 and having the next lowest signal value after A2 is the signal of the cartilage tip end A1 in FIG. 9.

Figure 11A:
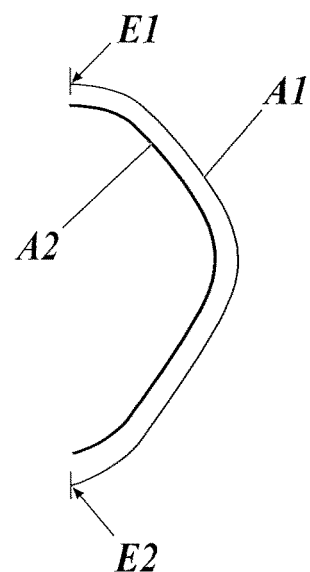
FIG. 11A schematically shows the state of a joint cartilage determined to be a score of 0 when the score is determined based on the length of the contour of the joint cartilage.

When creation of the profile ends, the pixel positions of A2 and A1 in the profile of each line are obtained (plotted on the x-y plane), whereby the contour of the bone tip end A2 and the contour of the cartilage tip end A1 are extracted. Then, the region sandwiched between the contour of the bone tip end A2 and the contour of the cartilage tip end A1 is extracted as the joint cartilage region. The positions of the start point E1 and the end point E2 of the contour of the cartilage tip end A1 (shown in FIG. 11A) are, for example, points of the cartilage tip end A1 contacting a straight line obtained by: drawing a circle having the largest arc part lying on the contour of the cartilage tip end A1, drawing the straight line in the x direction to pass through its center O, and rotating the straight line on the center O 90 degrees to each side. This is because, when one-dimensional gratings are used for imaging like the X-ray imaging device 1, signals of the contour extending in the x direction do not appear. When the gratings of the X-ray imaging device 1 are two-dimensional gratings or when the cartilage tip end is not parallel to the gratings but inclines with respect to the gratings and imaged, the start point and the end point of the joint cartilage region may be points when the straight line is rotated 150 degrees, 180 degrees or the like according to the imaging mode.

When A1 in the profile of each line is plotted, there may be a case where an isolated point not adjacent to A1 of an adjacent line is plotted as A1. This A1 is one detected by error, and the cartilage tip end A1 is not actually depicted (the contour is defective) in the line. Hence, the plotted A1 is deleted.

Now, return to FIG. 8. When the joint cartilage region is extracted, the extracted joint cartilage region is analyzed so that a feature value(s) of a predetermined type(s) is calculated (Step S13).

At Step S13, at least one of feature values of, for example, the length of the contour of the joint cartilage, the thickness of the joint cartilage, the difference value between the maximum value and the minimum value of the thickness of the joint cartilage and the area of the joint cartilage is calculated.

The length of the contour of the joint cartilage is calculated, for example, by counting the number of pixels of the contour of the cartilage tip end A1 and multiplying the counted number of pixels by the length for one pixel. The length for one pixel is, in the case of the Talbot-Lau imaging device which employs an enlargement imaging system, for example, "reciprocal of enlargement ratio×pixel size", the enlargement ratio being determined by the imaging position of a subject and the position of the X-ray detector 16 (distance between a subject and the X-ray detector 16), and varies depending on the imaging position of a subject. For example, when a subject is placed on the subject table 13 in a state of being on a jig, the thickness of the jig is taken into account for the enlargement ratio.

The thickness of the joint cartilage is calculated, for example, by, with respect to each line, drawing a straight line in a direction at right angles to the bone tip end A2 and counting the number of pixels from the bone tip end A2 to the intersection point of the straight line with the cartilage tip end A1, and multiplying the average value of the numbers of pixels counted with respect to the respective lines by the length for one pixel.

The difference value between the maximum value and the minimum value of the thickness of the joint cartilage is calculated, for example, first, by, with respect to each line, drawing a straight line in a direction at right angles to the bone tip end A2, counting the number of pixels from the bone tip end A2 to the intersection point of the straight line with the cartilage tip end A1 and multiplying the counted number of pixels by the length for one pixel, and then calculating the maximum value and the minimum value among the thicknesses calculated with respect to the respective lines and subtracting the minimum value from the maximum value.

The area of the joint cartilage is calculated by counting the number of pixels in the extracted joint cartilage region and multiplying the counted number of pixels by the area for one pixel. When the contour of the cartilage tip end A1 is defective, for example, the defective contour part is interpolated by interpolation, and the joint cartilage region is specified.

When calculation of the feature value ends, the calculated feature value is compared with a predetermined reference value(s), and a score indicating the state of the joint cartilage is determined (Step S14).

The joint cartilage is in the normal state when the contour thereof has: no defect; a predetermined value or more of thickness; uniform thickness; and no chipped piece. However, as arthritis or rheumatoid arthritis progresses, destruction of the joint cartilage is caused, and the contour of the joint cartilage may be defective, become thinner in thickness, become non-uniform in thickness and/or have a chipped piece. Hence, at Step S14, it is determined, based on the feature value calculated at Step S13, into which one of scores 0, 1 and 2, the state of the joint cartilage as the subject falls. The score 0 indicates that the joint cartilage is in the normal state. The score 1 indicates that destruction of the joint cartilage is at the first stage (the degree of destruction is lower than the second stage). The score 2 indicates that destruction of the joint cartilage is at the second stage (the destruction has further progressed). In the embodiment, the scores are 0 to 2. However, more reference values may be provided so that the scores can be of more stages.

For example, in the case where the feature value calculated at Step S13 is the length of the contour of the joint cartilage, the calculated length is compared with predetermined first reference value and second reference value. The first reference value is a value of the length of the contour of the cartilage tip end A1 when the contour of the joint cartilage is not defective, or a value of the length of the contour of the cartilage tip end A1 with a defective contour part interpolated by interpolation when the contour of the joint cartilage is defective. The "first reference value>second reference value>0" holds.

Figure 11B:
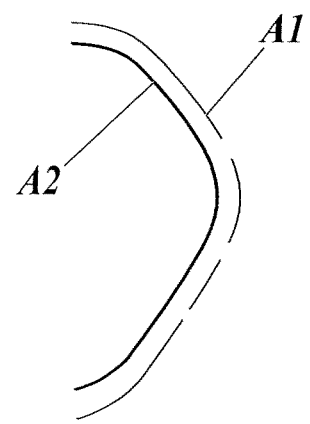
FIG. 11B schematically shows the state of a joint cartilage determined to be a score of 1 when the score is determined based on the length of the contour of the joint cartilage.
Figure 11C:
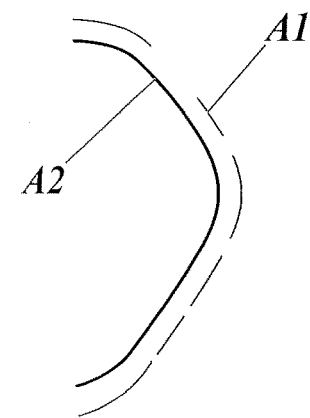
FIG. 11C schematically shows the state of a joint cartilage determined to be a score of 2 when the score is determined based on the length of the contour of the joint cartilage.

When the calculated length of the contour of the joint cartilage is equal to the first reference value (i.e. no defective part exists, see FIG. 11A), the score indicating the state of the joint cartilage is determined to be 0. When the "first reference value>the length of the contour of the joint cartilage≥second reference value" holds (see FIG. 11B), the score indicating the state of the joint cartilage is determined to be 1. When the "second reference value>the length of the contour of the joint cartilage" holds (see FIG. 11C), the score indicating the state of the joint cartilage is determined to be 2.

For example, in the case where the feature value calculated at Step S13 is the thickness of the joint cartilage, the calculated thickness is compared with predetermined first reference value and second reference value. The "first reference value>second reference value>0" holds.

Figure 12A:
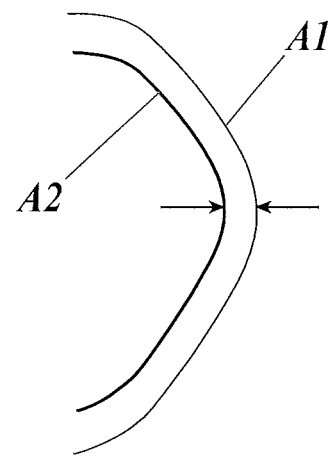
FIG. 12A schematically shows the state of a joint cartilage determined to be a score of 0 when the score is determined based on the thickness of the joint cartilage.
Figure 12B:
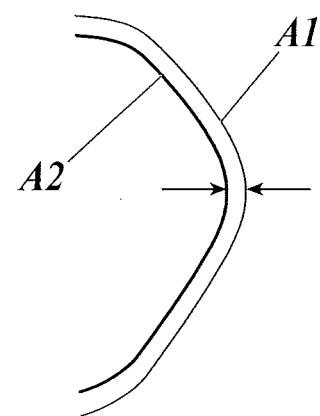
FIG. 12B schematically shows the state of a joint cartilage determined to be a score of 1 when the score is determined based on the thickness of the joint cartilage.
Figure 12C:
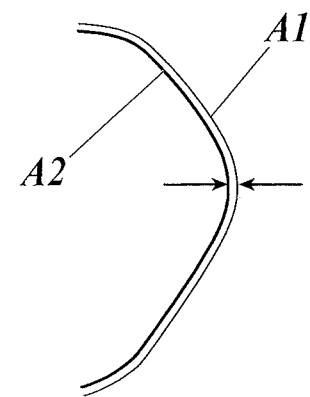
FIG. 12C schematically shows the state of a joint cartilage determined to be a score of 2 when the score is determined based on the thickness of the joint cartilage.

When the calculated thickness of the joint cartilage is equal to or more than the first reference value (see FIG. 12A), the score indicating the state of the joint cartilage is determined to be 0. When the "first reference value>the thickness of the joint cartilage>second reference value" holds (see FIG. 12B), the score indicating the state of the joint cartilage is determined to be 1. When the "second reference value>the thickness of the joint cartilage" holds (see FIG. 12C), the score indicating the state of the joint cartilage is determined to be 2.

For example, in the case where the feature value calculated at Step S13 is the difference value between the maximum value and the minimum value of the thickness of the joint cartilage, the calculated difference value is compared with predetermined first reference value and second reference value. The "first reference value>second reference value>0" holds.

Figure 13A:
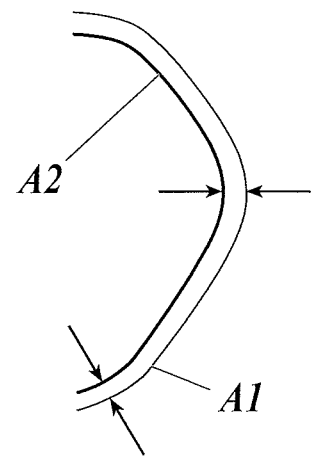
FIG. 13A schematically shows the state of a joint cartilage determined to be a score of 0 when the score is determined based on the difference value between the maximum value and the minimum value of the thickness of the joint cartilage.
Figure 13B:
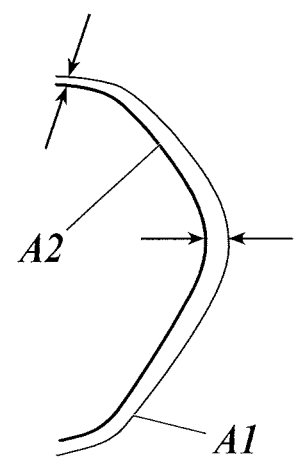
FIG. 13B schematically shows the state of a joint cartilage determined to be a score of 1 when the score is determined based on the difference value between the maximum value and the minimum value of the thickness of the joint cartilage.
Figure 13C:
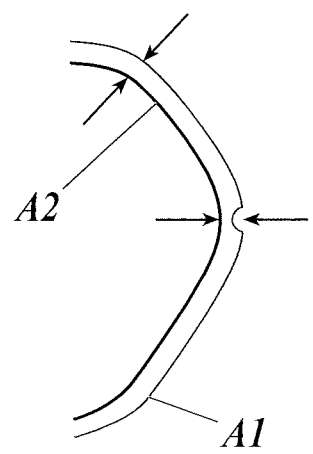
FIG. 13C schematically shows the state of a joint cartilage determined to be a score of 2 when the score is determined based on the difference value between the maximum value and the minimum value of the thickness of the joint cartilage.

When the calculated difference value is equal to or more than the first reference value (see FIG. 13A), the score indicating the state of the joint cartilage is determined to be 0. When the "first reference value>the difference value≥second reference value" holds (see FIG. 13B), the score indicating the state of the joint cartilage is determined to be 1. When the "second reference value>the difference value" holds (see FIG. 13C), the score indicating the state of the joint cartilage is determined to be 2.

For example, in the case where the feature value calculated at Step S13 is the area of the joint cartilage, the calculated area is compared with predetermined first reference value and second reference value. The "first reference value>second reference value>0" holds.

Figure 14A:
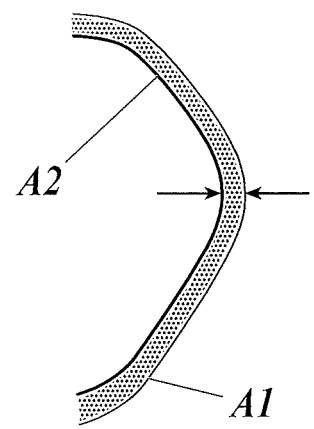
FIG. 14A schematically shows the state of a joint cartilage determined to be a score of 0 when the score is determined based on the area of the joint cartilage.
Figure 14B:
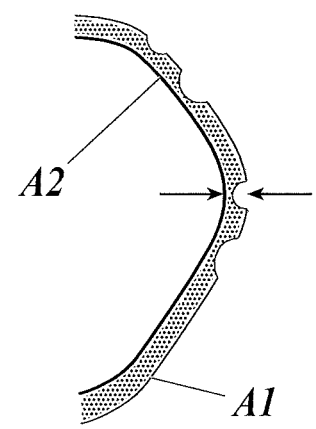
FIG. 14B schematically shows the state of a joint cartilage determined to be a score of 1 when the score is determined based on the area of the joint cartilage.
Figure 14C:
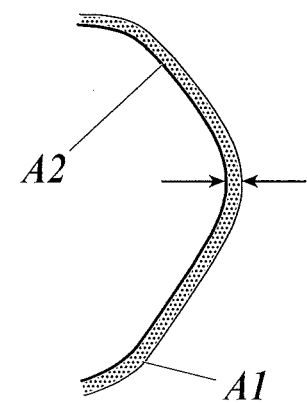
FIG. 14C schematically shows the state of a joint cartilage determined to be a score of 2 when the score is determined based on the area of the joint cartilage.

When the calculated area of the joint cartilage is equal to or more than the first reference value (see FIG. 14A), the score indicating the state of the joint cartilage is determined to be 0. When the "first reference value>the area of the joint cartilage>second reference value" holds (see FIG. 14B), the score indicating the state of the joint cartilage is determined to be 1. When the "second reference value>the area of the joint cartilage" holds (see FIG. 14C), the score indicating the state of the joint cartilage is determined to be 2.

The first reference value and the second reference value are different for each feature value.

In the above, explanation is made on the assumption that one joint is depicted in the differential phase image. However, in reality, a plurality of joints is often depicted in one image. In such a case, as explained above, the score determination process may be performed for each joint in the image so that the score for each joint is derived, or, for example, the overall score for a plurality of joints in the image, the overall score into which the states of the plurality of joints are integrated, may be derived, or both the score for each joint and the overall score may be derived. The overall score may be derived, for example, by comparing the sum of the feature values of the joints with a predetermined and prepared reference value(s) in the manner explained above, or may be derived from the scores for the respective joints (e.g. by calculating the average score).

Further, one joint may be imaged multiple times with the angle being changed, and the scores determined with respect to the respective differential phase images produced by the imaging performed multiple times may be integrated to be the score for the one joint. In this case, as a reference value(s) to compare, the same reference value(s) may be used for all the differential phase images with all the angles, or different reference values may be prepared for the respective differential phase images with the different angles. When the overall score for one joint is derived from the scores for the different angles, simple averaging may be performed. Alternatively, the overall score may be derived by weighting depending on the angles.

Now, return to FIG. 8. When determination of the score ends, the determined score and the differential phase image, which has been analyzed, are displayed on the display unit 53 (Step S15). Then, the score determination process ends.

As explained above, according to the controller 5, the control unit 51 generates at least a differential phase image based on an image signal(s) obtained by the X-ray imaging device 1 imaging a joint part, extracts a joint cartilage region based on the generated differential phase image, and analyzes the extracted joint cartilage region so as to calculate a feature value(s) indicating the state of the joint cartilage, and then compares the calculated feature value with a predetermined reference value(s), determines, based on the comparison result, into which one of predetermined scores of multiple stages the state of the joint cartilage falls, and displays the determination result on the display unit 53.

Consequently, a doctor who makes diagnosis can quantitatively understand the stage of the destruction state of the joint cartilage.

The score indicating the stage of the destruction state of the joint cartilage can be easily determined based on the feature value(s), such as the length of the contour of the joint cartilage, the thickness of the joint cartilage, the difference value between the maximum value and the minimum value of the thickness of the joint cartilage and/or the area of the joint cartilage.

In the above score determination process, as a mode of extracting the joint cartilage region based on the differential phase image, the joint cartilage region is directly extracted from the differential phase image, and the extracted joint cartilage region is analyzed so that the feature value indicating the state of the joint cartilage is calculated, and the score for the state of the joint cartilage is determined based on the calculated feature value. However, as another mode, it is possible that the joint cartilage region is extracted from an image generated by processing the differential phase image, and the extracted joint cartilage region is analyzed so that the feature value indicating the state of the joint cartilage is calculated, and the score for the state of the joint cartilage is determined based on the calculated feature value.

For example, it is possible that the joint cartilage region is extracted from a phase image generated by integration of the differential phase image, and the score is determined. As another example, it is possible that the joint cartilage region is extracted from an image generated by mathematical operation (addition or subtraction) of the differential phase image and at least one of an absorption image and a small-angle scattering image, and the score is determined. As another example, it is possible that the joint cartilage region is extracted from an image generated by mathematical operation of the differential phase mage and a differential absorption image generated by differentiation of an absorption image, and the score is determined.

Second Embodiment

Next, a second embodiment of the present invention is explained.

The configuration in the second embodiment is the same as that of the X-ray imaging device 1 explained in the first embodiment, and therefore the explanation is quoted.

In addition, the second embodiment is the same as the first embodiment in generating reconstructed images through the reconstructed image generation process shown in FIG. 6, and therefore the explanation is quoted.

In the second embodiment, a lesion is detected by performing a lesion detection process on a small-angle scattering image generated based on moire images obtained by imaging a joint part.

Here, a relationship between a signal value(s) of the small-angle scattering image and symptoms (outgrowths of synovial membrane and bone erosion) which can be seen in a lesion of rheumatoid arthritis or the like is explained. In the small-angle scattering image, the larger the X-ray scattering caused by a subject is, the lager (higher) the signal value is. In the embodiment, the signal value of the small-angle scattering image is in proportion to the display density of the image, and the larger the signal value is, the blacker the image is displayed, namely, the smaller the signal value is, the whiter the image is displayed.

Figure 15A:
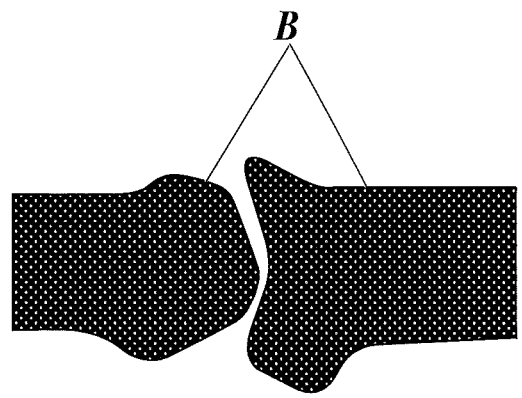
FIG. 15A schematically shows a small-angle scattering image having a normal joint part as a subject.

FIG. 15A to FIG. 16B each schematically show a small-angle scattering image generated based on moire images obtained by imaging a finger joint part. The small-angle scattering image has more gradation(s) (signal values, for example, 0 (white) to 1,023 (black)) than resolution(s) (for example, 0 to 255) of the monitor of the display unit 53. FIG. 15A and FIG. 15B each show the image obtained when the low signal side (for example, a range from 0 to 255) is displayed on the display unit 53, whereas FIG. 16A and FIG. 16B each show the image obtained when the high signal side (for example, a range from 768 to 1,023) is displayed.

Figure 15B:
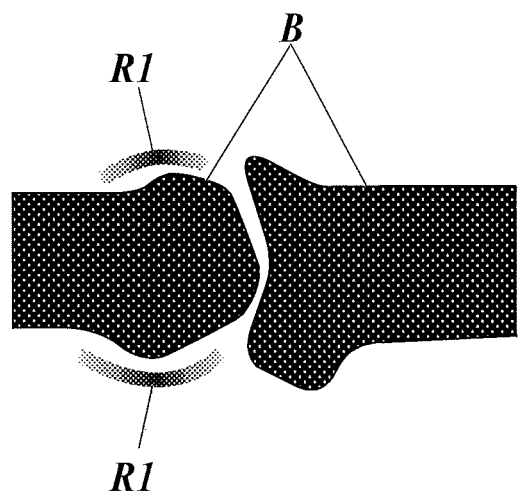
FIG. 15B schematically shows a small-angle scattering image having a joint part with outgrowths of synovial membrane as a subject.

FIG. 15A shows the small-angle scattering image (low signal side) having a normal joint part as a subject, whereas FIG. 15B shows the small-angle scattering image (low signal side) having a joint part with outgrowths of synovial membrane as a subject. As shown in FIG. 15A, in the small-angle scattering image (low signal side) having a normal joint part as a subject, a bone region(s) B is depicted blackish, and nothing is depicted outside the bone region B. On the other hand, as shown in FIG. 15B, in the small-angle scattering image (low signal side) having a joint part with outgrowths of synovial membrane as a subject, a blackish region(s) R1 is depicted outside the bone region B but within a predetermined distance from the bone region B. This region R1 is the signal indicating outgrowths of synovial membrane. The signal value of the region R1 is lower than the signal value of the bone region B (i.e. lower in density).

Figure 16A:
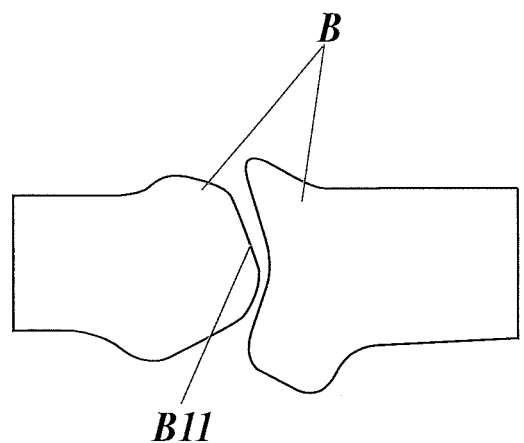
FIG. 16A schematically shows a small-angle scattering image having a normal joint part as a subject.
Figure 16B:
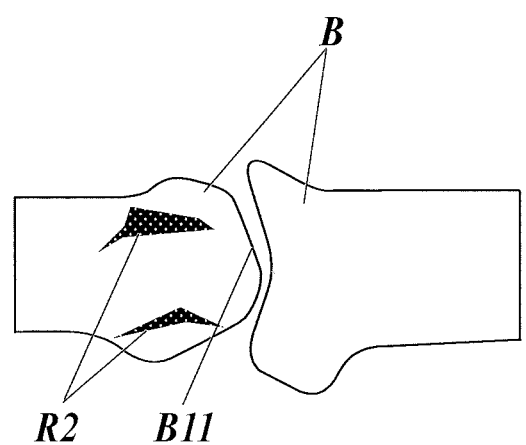
FIG. 16B schematically shows a small-angle scattering image having a joint part with bone erosion as a subject.

FIG. 16A shows the small-angle scattering image (high signal side) having a normal joint part as a subject, whereas FIG. 16B shows the small-angle scattering image (high signal side) having a joint part with bone erosion as a subject. As shown in FIG. 16A, in the small-angle scattering image (high signal side) having a normal joint part as a subject, nothing is depicted either inside or outside the bone region B. On the other hand, as shown in FIG. 16B, in the small-angle scattering image (high signal side) having a joint part with bone erosion as a subject, a blackish region(s) R2 is depicted near the joint (within a predetermined distance from the bone tip end B11) inside the bone region B. This region R2 is the signal indicating bone erosion.

That is, in the small-angle scattering image, the "signal value of outgrowths of synovial membrane<signal value of the bone region<signal value of bone erosion" holds. Hence, in the lesion detection process, outgrowths of synovial membrane and bone erosion are detected by binarizing the small-angle scattering image with a first threshold value for detection of outgrowths of synovial membrane and a second threshold value for detection of bone erosion.

The lesion detection process is performed by the controller 5 when imaging order information correlated with a reconstructed image(s) and having a finger joint part, a knee joint part or the like as a subject region is selected and lesion detection is instructed through the operation unit 52.

Figure 17:
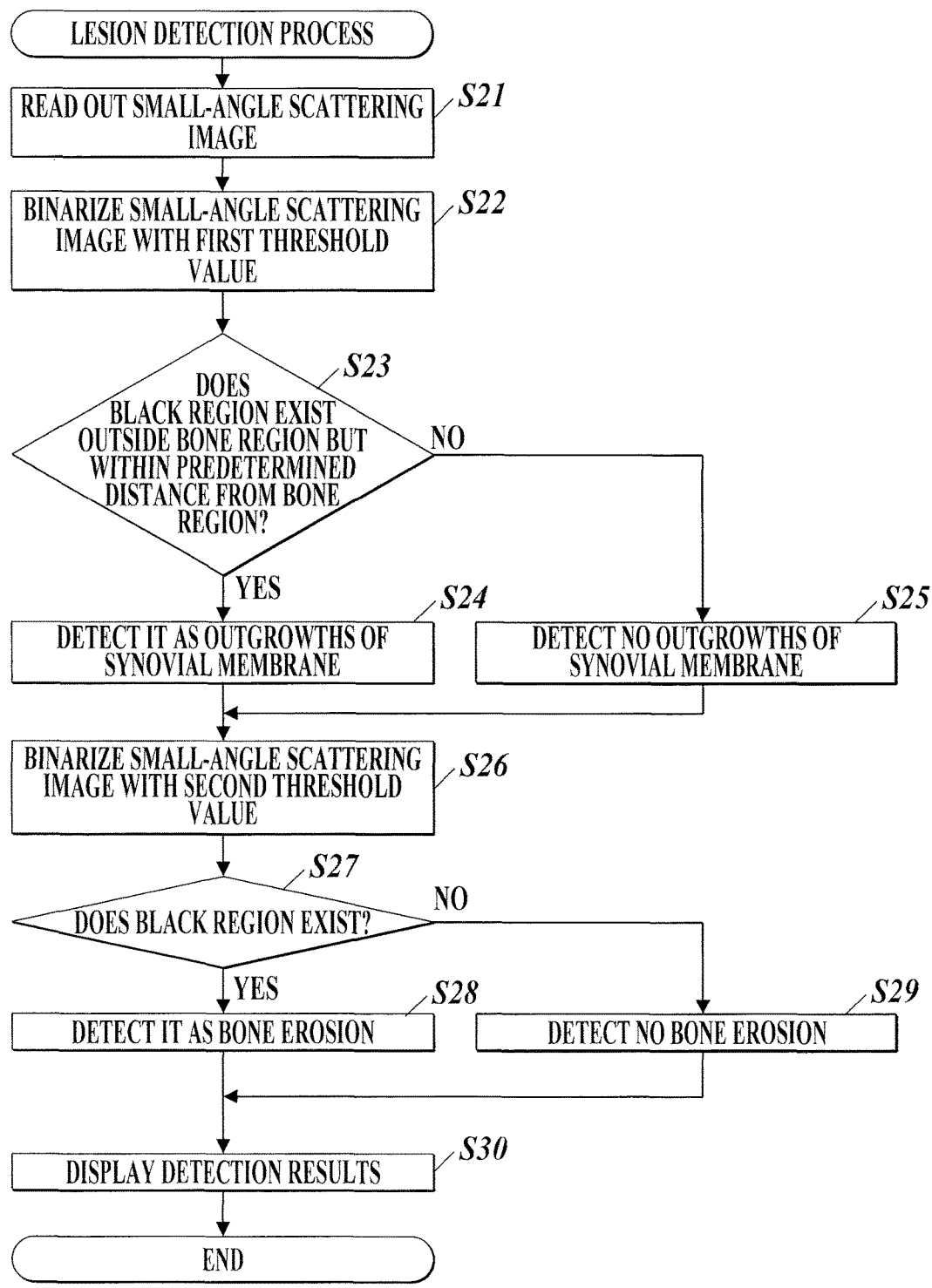
FIG. 17 is a flowchart of a lesion detection process performed by the control unit shown in FIG. 4.

FIG. 17 shows a flowchart of the lesion detection process performed by the control unit 51 of the controller 5. The lesion detection process is performed by the control unit 51 working together with the program(s) stored in the storage unit 55 according to the operation on the operation unit 52.

First, a small-angle scattering image correlated with the selected imaging order information is read from the storage unit 55 (Step S21).

Next, the read small-angle scattering image is binarized with a first threshold value for detection of outgrowths of synovial membrane (Step S22). The first threshold value is obtained experimentally and experientially. In the binarization, a signal value(s) exceeding the first threshold value is made to be a black region.

Next, it is determined whether or not, in the binarized image, a black region (a region having the signal value exceeding the first threshold value) exists outside a bone region but within a predetermined distance from the bone region (Step S23). The bone region can be specified from the binarized image, for example, by storing templates of images of bone regions for respective subject regions (e.g. a finger and a knee) in the storage unit 55 and performing template matching on the binarized image with a template for the subject region. Alternatively, a region determined as black may be specified as the bone region by additionally binarizing the small-angle scattering image read at Step S21 with a threshold value for detection of bones not to detect outgrowths of synovial membrane but to detect bones (first threshold value<threshold value for detection of bones).

When it is determined that, in the binarized image, a black region exists outside a bone region but within a predetermined distance from the bone region (Step S23; YES), the black region is detected as a region of outgrowths of synovial membrane, and this detection result (e.g. positional information on the detected region of outgrowths of synovial membrane) is stored in a memory of the control unit 51 (Step S24), and the process moves to Step S26. When it is determined that, in the binarized image, no black region exists outside a bone region but within a predetermined distance from the bone region (Step S23; NO), a notice of no detection of outgrowths of synovial membrane is stored in the memory of the control unit 51 (Step S25), and the process moves to Step S26.

At Step S26, the small-angle scattering image read at Step S21 is binarized with a second threshold value for detection of bone erosion (Step S26). The second threshold value is obtained experimentally and experientially, and the "second threshold value>first threshold value" holds. The second threshold value is experimentally and experientially a value higher than a value obtained experimentally and experientially as the signal value of the bone region. That is, the second threshold value is a threshold value not to detect bones but to detect bone erosion only. In the binarization, a signal value(s) exceeding the second threshold value is made to be a black region.

Next, it is determined that, in the image binarized at Step S26, whether or not a black region (a region having the signal value exceeding the second threshold value) exists (Step S27).

When it is determined that, in the image binarized at Step S26, a black region exists (Step S27; YES), the black region is detected as a region of bone erosion, and this detection result (e.g. positional information on the detected region of bone erosion) is stored in the memory of the control unit 51 (Step S28), and the process moves to Step S30.

When it is determined that, in the image binarized at Step S26, no black region exists (Step S27; NO), a notice of no detection of bone erosion is stored in the memory of the control unit 51 (Step S29), and the process moves to Step S30.

At Step S30, the detection results (outgrowths of synovial membrane has been detected or not and bone erosion has been detected or not) are displayed on the display unit 53 based on the information stored in the memory (Step S30). Then, the lesion detection process ends.

Thus, in the lesion detection process, outgrowths of synovial membrane and bone erosion, which are symptoms of a lesion of rheumatoid arthritis or the like, are detected, and the detection results are displayed. Consequently, a doctor can easily understand whether or not outgrowths of synovial membrane and/or bone erosion, which are symptoms of the lesion, exist.

In the above lesion detection process, as a simple method, the region exceeding the second threshold value is taken as the region of bone erosion. Alternatively, for detection of bone erosion, the following method may be used.

First, the small-angle scattering image read at Step S21 is binarized with the threshold value for detection of bones, and a region having the signal value exceeding the threshold value for detection of bones is specified as a bone region. Next, the small-angle scattering image read at Step S21 is binarized with the second threshold value, and when a region having the signal value exceeding the second threshold value exists in the region specified as the bone region (or within a predetermined distance from the bone tip end), the region is detected as bone erosion.

Further, the area of the detected region of outgrowths of synovial membrane and/or the area of the detected region of bone erosion may be measured, and the area(s) may be displayed together with the detection results. The area of the region of outgrowths of synovial membrane or bone erosion can be measured based on the number of pixels of the detected region. Thus, by measuring and displaying the area of the detected region, to what extent outgrowths of synovial membrane or bone erosion spreads can be shown to a doctor with a numerical value. Consequently, the doctor can quantitatively understand the level of the lesion.

In the above, the first embodiment and the second embodiment are explained. However, the descriptions in the above embodiments are preferred examples of the present invention, and the present invention is not limited thereto.

For example, in the above embodiments, used is the X-ray image system including the X-ray imaging device with the Talbot-Lau interferometer employing the system of moving the multi-slit 12 with respect to the first grating 14 and the second grating 15 in imaging. However, as an X-ray imaging device of a medical image system of the present invention, used may be an X-ray imaging device with a Talbot-Lau interferometer employing the system of moving one or both of the first grating 14 and the second grating 15, an X-ray imaging device with a Talbot interferometer employing the system of moving one of the first grating 14 and the second grating 15 with respect to the other thereof, or a medical imaging device 1A explained in a third embodiment.

Further, in the above embodiments, the score determination process and the lesion detection process are performed with the reconstructed images generated by the fringe scanning method. Alternatively, the score determination process and the lesion detection process may be performed with reconstructed images generated by the Fourier transform method.

Further, the detailed configurations and detailed actions of the devices constituting the X-ray image system can also be appropriately modified within the scope not departing from the spirit of the present invention.

Third Embodiment

Next, a third embodiment is explained.

Figure 18:
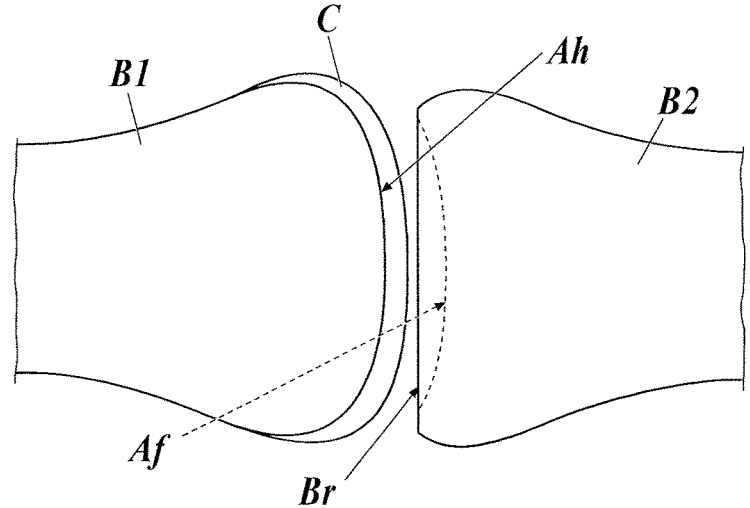
FIG. 18 schematically shows the structure of a joint part to explain the state of a joint part placed such that the articular head of one bone and the rim of the articular fossa of the other bone do not overlap.

A joint part is, as schematically shown in FIG. 18, formed of a bone B1 having an articular head Ah, the joint face of which is a convex, a bone B2 having an articular fossa Af, the joint face of which is a concave, and so forth, and the articular head Ah and the articular fossa Af are covered with cartilages C, respectively. In FIG. 18, only the cartilage C on the articular head Ah side is shown. In FIG. 9, the edge of this cartilage C is imaged with a streak (see A1 in FIG. 9).

The joint part is formed such that the curvature of the convex of the articular head Ah and the curvature of the concave of the articular fossa Af are the same (or approximately the same), whereby the cartilage C of the articular head Ah and the cartilage (not shown in FIG. 18) of the articular fossa Af smoothly slide over each other, and accordingly smooth flexing can be performed with the bone B1 and the bone B2.

If, as shown in FIG. 18, the joint part as a subject is placed such that the articular head Ah of one bone B1 and the rim Br of the articular fossa Af of the other bone B2 do not overlap when viewed from a radiation source (e.g. see 11*a* in FIG. 20 described below) of a medical imaging device, the edge of the cartilage C of the articular head Ah part of the bone B1 can be imaged without being shielded by the rim Br of the articular fossa Af of the other bone B2 (see FIG. 9).

Further, for example, as described below, if the space between the articular head Ah of the bone B1 and the articular fossa Af of the bone B2 can be extended by pulling the joint part, the cartilage C of the articular head Ah part of the bone B1 and the rim Br of the articular fossa Af of the bone B2 can be farther away from each other, and accordingly the edge of the cartilage C of the articular head Ah part of the bone B1 can be properly imaged without overlapping with and being shielded by the rim Br of the articular fossa Af of the other bone B2.

Figure 19A:
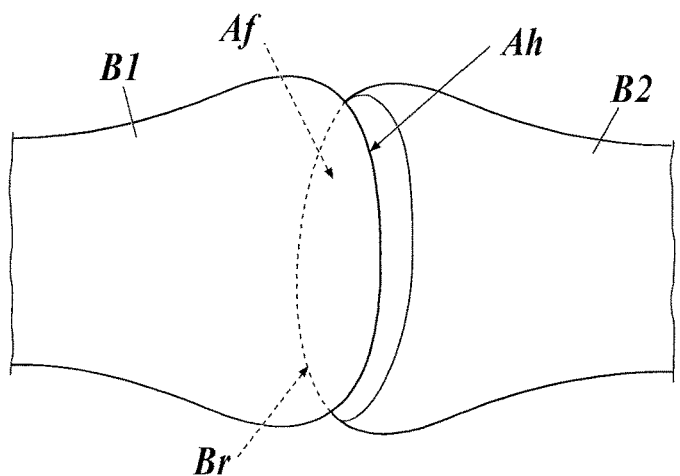
FIG. 19A is an illustration to explain the state of a joint part placed such that the articular head of one bone and the rim of the articular fossa of the other bone overlap.
Figure 19B:
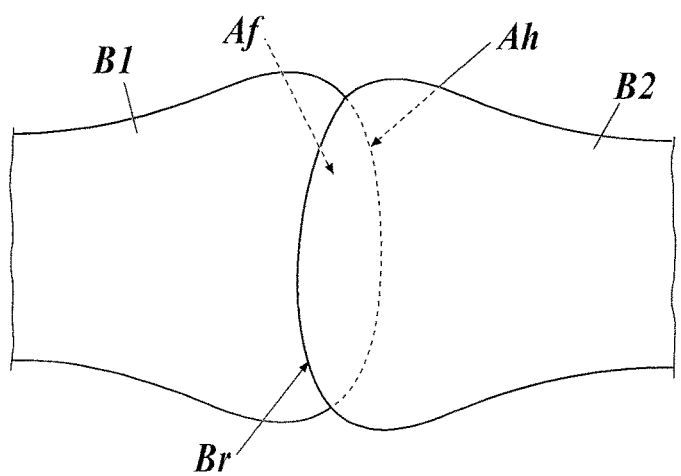
FIG. 19B is an illustration to explain the state of a joint part placed such that the articular head of one bone and the rim of the articular fossa of the other bone overlap.

However, as shown in FIG. 19A and FIG. 19B, if the joint part as a subject is placed such that the articular head Ah of the bone B1 and the rim Br of the articular fossa Af of the bone B2 overlap when viewed from the radiation source of the medical imaging device, the cartilage C of the articular head Ah part of the bone B1 overlaps with the rim Br of the articular fossa Af of the bone B2.

As shown in FIG. 9, particularly in a differential phase image, bones are imaged with contrast emphasized, so that, in the large contrast of the rim Br of the articular fossa Af of the bone B2, the signal of the cartilage C of the articular head Ah part of the bone B1, the cartilage C having small contrast (i.e. being imaged with a streak as shown in FIG. 9), is buried. Consequently, in the state shown in each of FIG. 19A and FIG. 19B, the cartilage C of the articular head Ah part of the bone B1 cannot be imaged.

Then, the inventors of this application and others have examined a medical imaging device which can well depict a cartilage of a joint part in a differential phase image reconstructed from moire images taken by an X-ray imaging device (called a "medical imaging device" in the third embodiment) with a Talbot interferometer or Talbot-Lau interferometer.

Hereinafter, the embodiment of the medical imaging device configured to well depict a cartilage of a joint part is explained, referring to the drawings.

In the embodiment, a medical imaging device 1A is the medical imaging device with a Talbot-Lau interferometer provided with a multi-slit (source grating) 12. The present invention is also applicable to a medical imaging device with a Talbot interferometer provided with a first grating (also called a "G1 grating") 14 and a second grating (also called a "G2 grating") 15 without a multi-slit 12.

Figure 20:
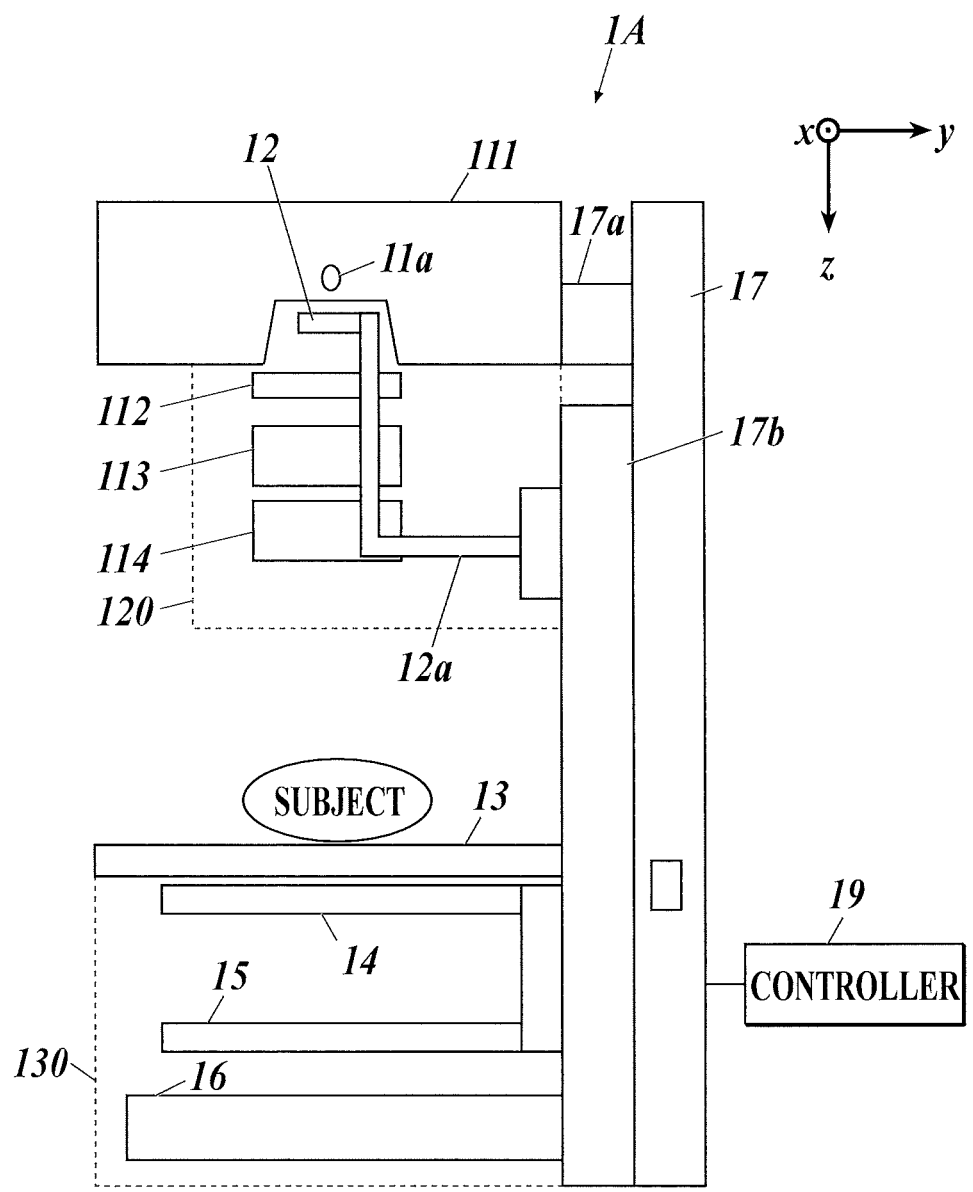
FIG. 20 is a schematic view showing the overall image of a medical imaging device according to a third embodiment.

FIG. 20 is a schematic view showing the overall image of the medical imaging device 1A according to the embodiment. The medical imaging device 1A of the embodiment includes, as shown in FIG. 20, a radiation generating device 11, a multi-slit 12, a subject table 13, a first grating 14, a second grating 15, an X-ray detector (radiation detector) 16, a holding unit (prop) 17 and a controller 19.

The medical imaging device 1A is, what is called, a vertical type, and the radiation generating device 11, the multi-slit 12, the subject table 13, the first grating 14, the second grating 15 and the X-ray detector 16 are arranged in this order in the gravity direction which is the z direction. That is, in the embodiment, the z direction is the emission direction of the radiation from the radiation generating device 11.

In the embodiment, as shown in FIG. 20, the medical imaging device 1A emits radiation downward to a subject from the radiation generating device 11 provided on the upper side. However, the radiation emission direction is not limited to from the upper side downward, and hence radiation may be emitted in a horizontal direction or any appropriate direction. The present invention is applicable to these cases too.

The medical imaging device 1A performs imaging with the principles of the Talbot-Lau interferometer constituted of the multi-slit 12 provided in the Talbot interferometer, which is explained with FIG. 5 in the first embodiment.

A radiation source 11a of the medical imaging device 1A corresponds to the X-ray source 11 in FIG. 1. The components of the medical imaging device 1A having the same names and same reference numbers as those in the first and second embodiments have the same functions and configurations as those in the first and second embodiments. However, in the medical imaging device 1A, the holding unit (prop) 17 is provided parallel to the arrangement direction (x direction) of the slits S shown in FIG. 2, whereas, in the X-ray imaging device 1 shown in FIG. 1, the holding unit 17 is provided parallel to the extending direction (y direction) of the slits S shown in FIG. 2.

In the medical imaging device 1A, as shown in FIG. 20 for example, the first grating 14, the second grating 15 and the X-ray detector 16 are provided in a second cover unit 130. The second cover unit 130 is provided for the first grating 14, the second grating 15, the X-ray detector 16 and so forth not to be kicked/hit or touched by a leg of a patient or the like, thereby protecting the X-ray detector 16 and so forth.

In the embodiment, the medical imaging device 1A takes a plurality of moire images by, what is called, the fringe scanning method. That is, the medical imaging device 1A of the embodiment takes a plurality of moire images while shifting the relative position of the first grating 14 and the second grating 15 in the x axis direction (i.e. the direction at right angles to the extending direction of the slits S (y axis direction)) in FIG. 2, FIG. 5 or FIG. 20.

Figure 21:
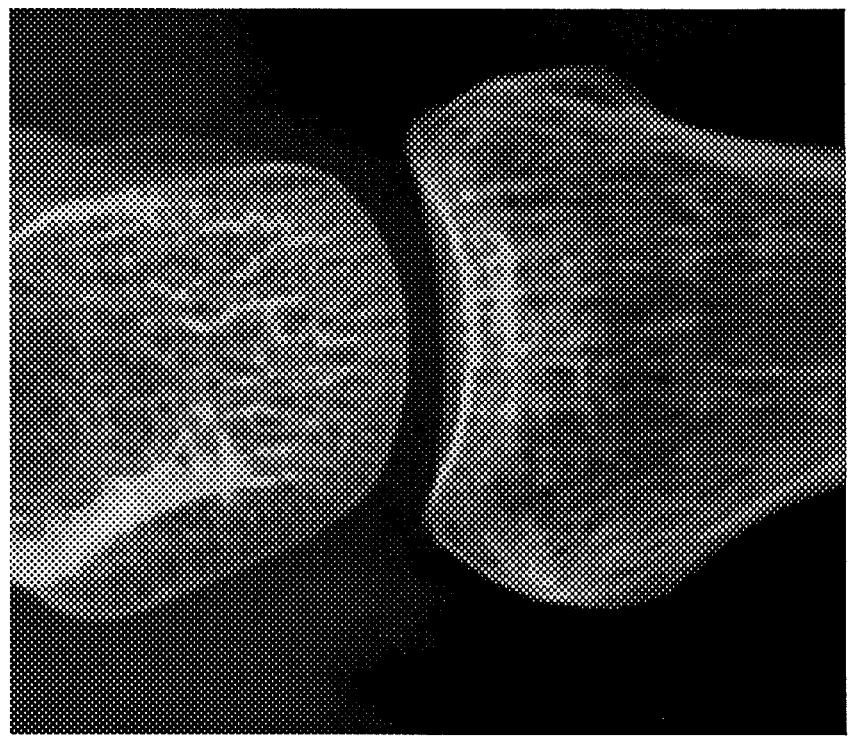
FIG. 21 is a picture showing an example of a radiation absorption image in which a joint part is imaged.

Then, a not-shown image processing device which receives image signals of the moire images from the medical imaging device 1A performs image processing thereon and reconstructs an image such as an absorption image shown in FIG. 21, a differential phase image shown in FIG. 9 and/or a not-shown small-angle scattering image based on the moire images.

In order that the medical imaging device 1A of the embodiment takes a plurality of moire images by the fringe scanning method, a not-shown moving device or the like to move the first grating 14 in the y axis direction by predetermined amount is provided. Instead of moving the first grating 14, the medical imaging device 1A may be configured to move the second grating 15 or to move both of them.

It is possible that the medical imaging device 1A takes only one moire image with the relative position of the first grating 14 and the second grating 15 fixed, and the image processing device performs image processing thereon and analyzes this moire image by the Fourier transform method or the like so as to reconstruct an absorption image, a differential phase image or the like.

When this method is used, it is unnecessary for the medical imaging device A1 to be provided with the above-described moving device or the like. The present invention is applicable to a medical imaging device not provided with such a moving device too.

In the embodiment, the multi-slit 12 is provided under the radiation generating device 11. In order not to transmit vibrations of the radiation generating device 11 to the multi-slit 12, the vibrations being caused by rotation of the anode of the radiation source 11a or the like, in the embodiment, the multi-slit 12 is not attached to the radiation generating device 11 but is attached to a fixing member 12a attached to a base unit 17b provided on the holding unit 17.

In the embodiment, in order not to propagate the vibrations of the radiation generating device 11 to the other part of the medical imaging device 1A, such as the holding unit 17 (or in order to make the vibrations to propagate smaller), a buffer member 17a is provided between the radiation generating device 11 and the holding unit 17.

To the above-described fixing member 12a, in addition to the multi-slit 12, a filtration filter (also called an "added filter") 112 to change the quality of the radiation having passed through the multi-slit 12, an irradiation field aperture stop 113 to reduce the irradiation field of the emitted radiation, an irradiation field lamp 114 to perform positioning by emitting visible light so as to irradiate a subject therewith instead of radiation before the radiation is emitted, and so forth are attached.

It is unnecessary for the multi-slit 12, the filtration filter 112 and the irradiation field aperture stop 113 to be provided in this order. In the embodiment, around the multi-slit 12 and so forth, a first cover unit 120 to protect them is provided.

The controller 19 (see FIG. 20) is, in the embodiment, constituted of a computer which includes a CPU (Central Processing Unit), a ROM (Read Only Memory), a RAM (Random Access Memory) and an input/output interface connected with each other via a bus (all not shown). The controller 19 may be configured not as a general-use computer such as that in the embodiment but as a special control device. In addition, although not shown, the controller 19 is provided with appropriate units or devices such as an input unit and a display unit.

The controller 19 controls the medical imaging device 1A overall. That is, for example, the controller 19 is connected to the radiation generating device 11 and can set a tube voltage, a tube currency, emission time and so forth for the radiation source 11a. Further, the controller 19 may be configured, for example, to relay transmission/reception of signals and data between the X-ray detector 16 and a not-shown external image processing device (e.g. the controller 5 in the first and second embodiments).

When the medical imaging device 1A is configured to take a plurality of moire images by the fringe scanning method as with the embodiment, the controller 19 is configured to control the above-described moving device so as to adjust the predetermined amount to move the first grating 14 (or the second grating 15 or both of them), adjust timing of the movement of the grating and the emission of the radiation from the radiation generating device 11, and so forth.

It is possible that as a controller to control the radiation generating device 11, a generator dedicated to the radiation generating device 11 is used, and the controller 19 to control the moving device to move the grating or the like is configured as a device different from the generator for the radiation generating device 11. The controller 19 can be configured appropriately.

The controller 19 may have an image processing function like the controller 5 in the first and second embodiments. More specifically, the controller 19 may have a function to perform image processing such as the reconstructed image generation process and the score determination process, which are explained in the first embodiment, and the lesion detection process, which is explained in the second embodiment.

[Regarding Fixing Unit]

In order to image a cartilage C (see FIG. 18) of a joint part of a patient as a subject in a differential phase image, as described above, a joint part of a patient as a subject needs to be placed on the subject table 13 not as shown in FIGS. 19A and 19B where the articular head Ah of the bone B1 and the rim Br of the articular fossa Af of the bone B2 overlap but as shown in FIG. 18 where the articular head Ah of the bone B1 and the rim Br of the articular fossa Af of the bone B2 do not overlap when viewed from the radiation source 11a (see FIG. 20) of the medical imaging device 1A.

Then, in the medical imaging device 1A of the embodiment, in order to place the joint part of the patient as the subject on the subject table 13 in such a state, the subject table 13 is provided with a fixing unit which fixes the position of a joint part with respect to the radiation emitted from the radiation generating device 11 and can adjust the angle formed of the bone B1 and the bone B2 of the joint part.

Hereinafter, configuration examples of the fixing unit are explained. Further, action of the medical imaging device 1A of the embodiment is also explained.

Hereinafter, a plurality of bones constituting a joint part are expressed as the thorax side (i.e. the trunk side) and the periphery side (i.e. the limb side). That is, for example, in the case of a finger joint part, the bone on the palm side is the thorax side, and the bone on the finger side is the periphery side. As another example, in the case of a knee joint part, the femur is the thorax side, and the tibia and the fibula are the periphery side.

In the medical imaging device 1A of the embodiment, the subject table 13 is provided with the fixing unit which fixes the positions of the thorax side and the periphery side of a joint of a patient as a subject with respect to the radiation emitted from the radiation generating device 11, and the fixing unit is configured to adjust the angle formed of the thorax side and the periphery side of the joint part.

First Configuration Example

Figure 22:
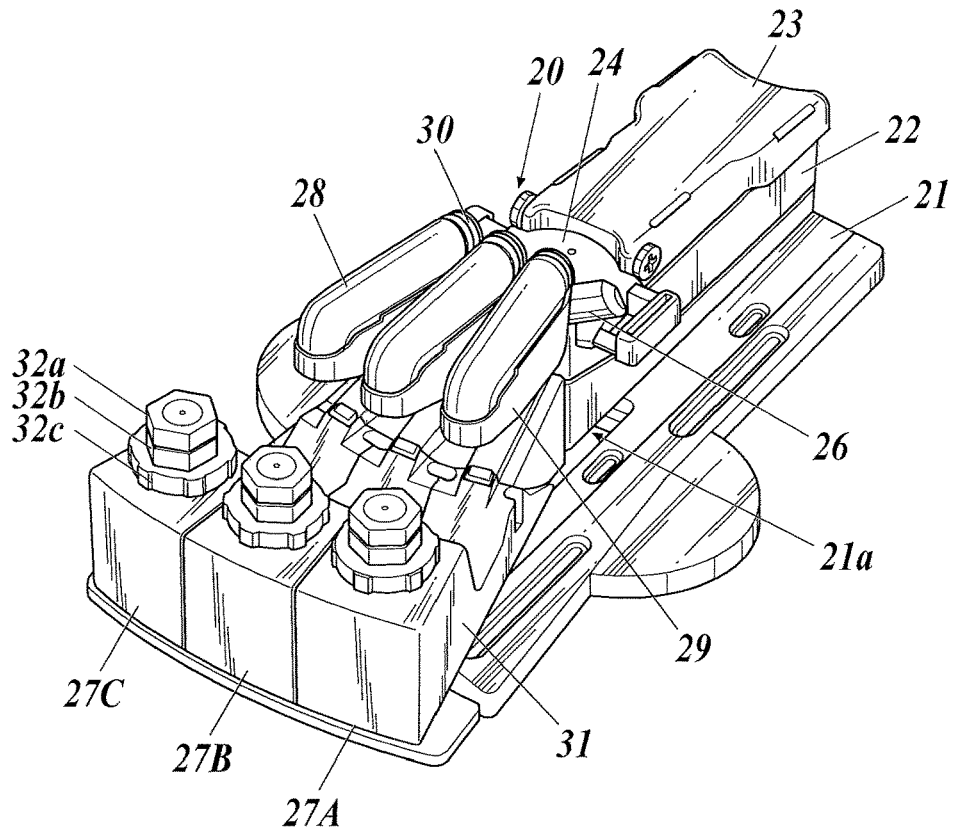
FIG. 22 is a perspective view showing a first configuration example of a fixing unit.
Figure 23:
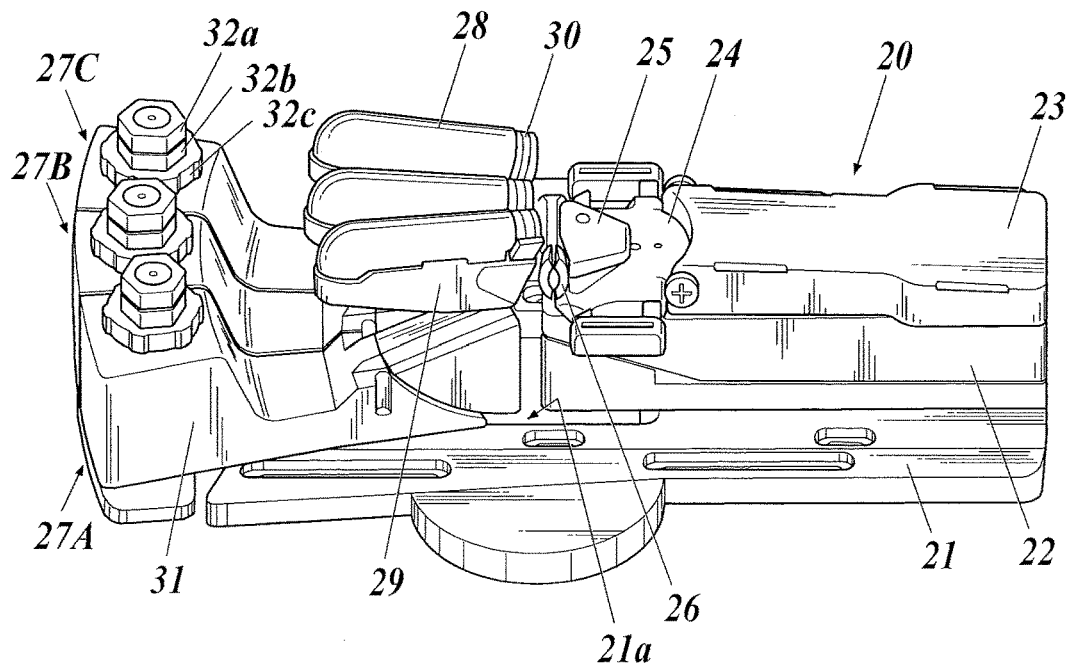
FIG. 23 is a perspective view showing the first configuration example of the fixing unit.

FIG. 22 and FIG. 23 are perspective views each showing a first configuration example of the fixing unit. In the first configuration example, a fixing unit 20 to perform position fixing and angle adjustment of a finger joint part is explained.

Hereinafter, as the fixing unit 20 of the first configuration example, a fixing unit used for imaging a joint part constituted of a metacarpal as the thorax side and a proximal phalange as the periphery side (i.e. the joint (MP joint) part at the base of a finger) is explained. However, by having the same configuration and modifying the configuration a little, a fixing unit used for imaging a joint part constituted of a proximal phalange as the thorax side and an intermediate phalange as the periphery side (i.e. the second joint (PIP joint) of a finger), a joint part constituted of an intermediate phalange as the thorax side and a distal phalange as the periphery side (the first joint (DIP joint) of a finger), a wrist joint part or the like can be configured.

Further, hereinafter, in order to make explanation easy, in the first configuration example, the periphery side of a finger of a patient placed (i.e. the fingertip side, the lower left side in FIG. 22 and the left side in FIG. 23) is referred to as the front, and the thorax side of the finger of the patient placed (i.e. the wrist or forearm side, the upper right side in FIG. 22 and the right side in FIG. 23) is referred to as the rear.

The fixing unit 20 is placed on the subject table 13 (see FIG. 20) of the medical imaging device 1A so as to be used. The fixing unit 20 is placed at an appropriate position on the subject table 13, whereby the positions of the thorax side and the periphery side of a joint part of a patient fixed on the fixing unit 20 are fixed at appropriate positions with respect to the radiation emitted from the radiation generating device 11. In order that the fixing unit 20 does not slip on the subject table 13, the lower face (the bottom) of a base 21 of the fixing unit 20 may be provided with a nonslip member or the like, for example.

As shown in FIG. 22 and FIG. 23, in the fixing unit 20, a pedestal part 22 is provided from the rear end side of the near-flat plate-shaped base 21 to approximately the center part thereof. Over the rear end side of the pedestal part 22, a placement table 23 where a wrist and/or a forearm part is placed is provided. Although not shown, the pedestal part 22 and the placement table 23 are provided with, for example, belt-shaped fixtures to fix a wrist, a forearm part or the like of a patient placed on the placement table 23.

The front end side of the pedestal part 22 (approximately the center part of the base 21 of the fixing unit 20) is provided with a concave part 24 which slightly becomes hollow downward from the placement table 23. In the concave part 24 of the pedestal part 22, a palm can be housed to face downward. At a position in the concave part 24 corresponding to the position of the hollow at the center of the palm placed to face downward, a convex part 25 is provided to be convex upward.

The size of a palm is different depending on the physical build, age, sex and so forth of a patient. Hence, in the fixing unit 20 of the first configuration example, the placement table 23 is configured to be movable in the front-rear direction in relation to the pedestal part 22, whereby the position of the placement table 23 in relation to the pedestal part 22 can be adjusted and fixed to be suitable for the size or the like of a palm of a patient.

Although not shown, the placement table 23 may be formed of a plurality of plate-shaped members, so that the concave part 24 can change its shape optimal to the size of a palm by the number of plate-shaped members being changed. Further, the convex part 25 may be attachable/detachable so as to be suitable for the size of a palm, and still further, the convex part 25 may slide in the front-rear direction to adjust its position.

Further, for example, the pedestal part 22 may be detachable, or the angle of the placement table 23 to the pedestal part 22 in the up-down direction may be changeable, whereby the angle of an arm of a patient can be changed. Any other configurations or the like to fit a finger of a patient into the fixing unit 20 of the first configuration example can be appropriately adopted.

Meanwhile, a side of the upper side of the front end of the pedestal part 22 (i.e. the front end of the concave part 24) is provided with a projecting part 26 sideways. This projecting part 26 is provided at a position which touches a portion between the index finger and the thumb which naturally hangs downward (i.e. the fork between the fingers) in a state in which a palm is housed in the concave part 24 and the fingers and so forth are inserted into finger holding members 28a, which are described below, and so forth. The projecting part 26 is directly fixed to the pedestal part 22.

As described below, when the fingers fixed by the finger holding members 28 and so forth are pulled forward, the palm, the wrist and so forth are also pulled and intend to move forward. However, this projecting part 26 is engaged with the fork between the index finger and the thumb, and the above-described convex part 25 is engaged with the hollow at the center of the palm, whereby the palm and so forth are prevented from moving forward. The convex part 25 is preferably formed of a soft and hardly-slipping material such as silicon. Further, bumps or the like to prevent slippage may be formed on the surface thereof.

Thus, when pulling a finger(s), the fixing unit 20 of the first configuration example having such a configuration can properly pull the finger to extend the space between the thorax side and the periphery side of a joint part, namely, in the above case, the space between the metacarpal as the thorax side and the proximal phalange as the periphery side. Further, because the fixing unit 20 prevents a finger(s) and so forth of a patient from moving forward by engaging the finger and so forth at multiple points, for example, with the projecting part 25 and the convex part 26, the force applied to the fingers of the patient is dispersed, so that that the patient does not feel pain as compared with the case of preventing a finger(s) and so forth of a patient from moving forward by engaging the finger and so forth at one point.

Meanwhile, the fixing unit 20 of the first configuration example is provided with jig units 27A to 27C on the base 21 in front of the pedestal part 22 for the index finger, the middle finger and the ring finger, respectively, so as to adjust the angles of the fingers, pull the fingers and so forth.

In FIG. 22 and FIG. 23, the jig units 27A to 27C are provided for the index finger, the middle finger and the ring finger, namely, one for each and three in total. However, there may also be provided jig units for the thumb and the little finger. Hereinafter, when the jig units 27A to 27C are explained not separately but generally, they are called the jig unit(s) 27.

The jig units 27A to 27C have the same configuration, but act independently from each other.

More specifically, the jig units 27A to 27C are independently turnable in the horizontal direction (right-left direction) with respect to the base 21 centering on their respective rear end parts (i.e. the side close to the pedestal part 22) and can be fixed at positions to which they have turned, whereby, for example, the space between the index finger and the middle finger can be extended to right and left, or the spaces between the three fingers can be extended.

On each jig unit 27, the finger holding member 28 like a fingerstall to insert a finger of a patient is provided at a position where the finger can be inserted when the finger is stretched forward with the palm housed in the concave part 24 of the pedestal part 22 as described above. The finger holding member 28 is supported from underneath by a support member 29.

The finger holding member 28 is preferably formed to be transparent (no color or a color such as grey) so that the finger inserted therein can be seen. Further, in order to prevent the inside of the finger holding member 28 from not being seen because of steams from sweat of a patient, the finger holding member 28 is preferably provided with a slit-shaped hole(s) on the lateral face or the like, for example. Further, the finger holding member 28 may be formed in the shape of a cover so as to cover a finger from the above, instead of being formed like a fingerstall.

The circumference of the rear end part of the finger holding member 28 is provided with a belt 30 which is attached to the support member 29 so as to tightly fasten and fix the finger inserted in the finger holding member 28. On the front end side of a base part 31 of the jig unit 27, the base part 31 being provided below the finger holding member 28 and so forth, three independently rotatable dials 32a to 32c of a three-layer structure in the up-down direction are provided. For example, by rotating the dial 32a at the top, a finger is tightly fastened with the belt 30 or the tight fastening with the belt 30 is released.

Thus, in the fixing unit 20 of the first configuration example, the joint part to be imaged, namely, in the first configuration example, the joint part constituted of the metacarpal as the thorax side and the proximal phalange as the periphery side (i.e. the joint part at the base of a finger), is placed over the space provided between the pedestal part 22 on the rear side and the jig units 27A to 27C on the front side in a state in which the palm is housed in the concave part 24 to face downward and the finger is inserted in the finger holding member 28 and tightly fastened with the belt 30.

As shown in FIG. 22 and FIG. 23, at a part of the base 21 under the position where the joint part to be imaged is placed, namely, at a part of the base 21 corresponding to the space between the pedestal part 22 and the jig units 27A to 27C, an opening part 21a is provided. This can prevent a joint part from being imaged with the components constituting the fixing unit 20 overlapping with the joint part and also prevent the components constituting the fixing unit 20 from being imaged into the surrounding of the joint part when the joint part is imaged with the radiation emitted from the above to produce moire images.

The base 21 may be formed of a material having a low transmissivity of radiation, such as metal, or may be formed by sticking a plate-shaped member having a low transmissivity of radiation, such as lead, to the base 21 formed of resin or the like. The base 21 thus configured can surely prevent images of the components constituting the fixing unit 20 from being imaged into moire images or a differential phase image or the like reconstructed therefrom.

Consequently, the taken or reconstructed images do not produce a sense of discomfort, and also the unexpected appearance of the components constituting the fixing unit 20 being an obstacle to perform image processing can be surely prevented.

The finger holding member 28 and the support member 29 are, for example, pasted together to move integrally. The rear end of a not-shown support which is provided in the support member 29 so as to support the support member 29 is pivotally held at the rear end of the base part 31 of the jig unit 27 so as to be turnable in the up-down direction.

By rotating, for example, the second dial 32b from the top among the dials 32a to 32c on the front end side of the base part 31 of the jig unit 27, the support of the support member 29 can be turned in the up-down direction with respect to the base part 31 of the jig unit 27 while the angle of the support of the support member 29 to the base part 31 is adjusted. Further, by stopping the rotation of the dial 32b, the support of the support member 29 can be fixed at a position to which the support has turned.

By turning the support of the support member 29 in the up-down direction while adjusting the angle thereof to the base part 31 of the jig unit 27, the support member 29 and the finger holding member 28 are turned in the up-down direction, so that a finger of a patient inserted in the finger holding member 28 is turned in the up-down direction while the angle thereof to the base part 31 of the jig unit 27 is adjusted.

As described above, the joint part, the position of which is fixed to the fixing unit 20 on the subject table 13 (see FIG. 20), to be imaged is constituted of the metacarpal as the thorax side having the articular head Ah (see FIG. 18, etc.) and the proximal phalange as the periphery side having the articular fossa Af. The first joint (DIP joint) and the second joint (PIP joint) are each also constituted of the thorax side having the articular head Ah and the periphery side having the articular fossa Af.

Hence, the fixing unit 20 configured as described above can turn the periphery side having the articular fossa Af in the up-down direction among the thorax side and the periphery side of a joint part, and can adjust the angle formed of the thorax side and the periphery side of the joint part by adjusting the angle of the side (i.e. the periphery side in this case) having the articular fossa Af.

Further, the fixing unit 20 thus configured can adjust the angle of the side having the articular fossa Af with respect to the emission direction (i.e. the z axis direction) of the radiation emitted from the radiation generating device 11 (see FIG. 20) by adjusting the angle of the side having the articular fossa Af in the up-down direction among the thorax side and the periphery side of a joint part.

Thus, by adjusting the angle of the side (the periphery side in this case) having the articular fossa Af in the up-down direction, the joint part can be placed as shown in FIG. 18 where the articular head Ah of the bone B1 (the thorax side (metacarpal) in this case) and the rim Br of the articular fossa Af of the bone B2 (the periphery side (proximal phalange) in this case) do not overlap when viewed from the radiation generating device 11.

In the actual imaging, the fixing unit 20 is placed on the subject table 13 (see FIG. 20) of the medical imaging device 1A, a joint part of a patient as a subject is fixed to the fixing unit 20 as described above, the finger is tightly fastened with the belt 30, and the angle of the finger in the up-down direction is adjusted and fixed. Then, the position of the fixing unit 20 on the subject table 13 is adjusted such that radiation is properly emitted from the radiation generating device 11 to the joint part.

By irradiating the subject, namely, the joint part of the patient, fixed to the fixing unit 20 on the subject table 13, with the radiation, moire images can be taken in a state in which the articular head Ah of the bone (metacarpal) B1 does not overlap with the rim Br of the articular fossa Af of the bone (proximal phalange) B2 and accordingly is not shielded by the rim Br of the articular fossa Af of the bone (proximal phalange) B2.

By reconstructing, for example, a differential phase image based on thus-taken moire images, as shown in FIG. 9 and FIG. 18 for example, the edge (see A1 in FIG. 9) of the cartilage C of the articular head Ah of the bone (metacarpal) B1 can be well imaged in the differential phase image.

The medical imaging device 1A configured to take a plurality of moire images by the above-described fringe scanning method can, as described above, properly fix a joint part of a patient to the fixing unit 20 and surely prevent the subject from moving while taking moire images. Consequently, moire images of a subject with no movement thereof can be taken. Therefore, the edge of the cartilage C of the articular head Ah of the bone B1 can be well imaged in a differential phase image without being blurred.

Further, in order to adjust, before taking moire images, the angle of a finger in the up-down direction such that the articular head Ah of the bone (metacarpal) B1 and the rim Br of the articular fossa Af of the bone (proximal phalange) B2 do not overlap, for example, a moire image(s) is taken with weak radiation emitted from the radiation generating device 11 to the joint part fixed to the fixing unit 20 on the subject table 13. In this case, it is possible that only one moire image is taken, and a radiologist or the like adjusts the angle of the finger in the up-down direction to an appropriate angle, looking at the taken moire image, or the moire image(s) is taken as a video, and a radiologist or the like adjusts the angle of the finger in the up-down direction to an appropriate angle, looking at the taken moire image as the video. Thus, the angle of a finger in the up-down direction can be properly adjusted.

It is troublesome for a radiologist to adjust the angle of a finger in the up-down direction in the fixing unit 20 each time the medical imaging device 1A images a joint part thereof. Hence, the fixing unit 20 is preferably configured to measure the adjusted angle of a finger in the up-down direction.

In order that the fixing unit 20 is configured to measure the adjusted angle of a finger in the up-down direction, for example, the dial 32b (see FIG. 22 or FIG. 23) to adjust the angle of a finger in the up-down direction may be graduated in numerical values of angle which increases in the rotational direction with 0° at the start point of the rotation of the dial 32b or provided with a display unit to display angle which increases or decreases according to the amount of the rotation of the dial 32b, for example.

By measuring and recording the angle of a finger in the up-down direction when adjusting the angle, the angle of the finger in the up-down direction can be properly adjusted from the next imaging without adjusting the angle of the finger in the up-down direction in the manner described above again, namely, only by making the angle of the finger in the up-down direction agree with the previously measured and recorded angle. Therefore, the angle of a finger in the up-down direction can be very easily adjusted and also properly adjusted.

Meanwhile, in the fixing unit 20, by rotating, for example, the dial 32c at the bottom among the dials 32a to 32c on the front end side of the base part 31 of the jig unit 27, a finger of a patient inserted in the finger holding member 28 and tightly fastened with the belt 30 is pulled forward, and accordingly the joint part can be pulled in the direction to extend the space between the thorax side and the periphery side.

More specifically, by rotating the dial 32c, the support member 29 is moved forward together with the finger holding member 28 and the belt 30 with respect to the above-described not-shown support of the support member 29, so that a finger of a patient inserted in the finger holding member 28 and tightly fastened with the belt 30 is moved forward.

Then, at the time, as described above, regarding the palm side of the patient, the fork between the index finger and the thumb is engaged with the projecting part 26, and the hollow at the center of the palm is engaged with the convex part 25, whereby forward movement thereof is prevented. Thus, by rotating the dial 32c, a joint part can be pulled in the direction to extend the space between the thorax side and the periphery side.

Further, in this case too, by stopping the rotation of the dial 32c, the support member 29 can be fixed at a position to which the support member 29 has moved forward, and the state in which the joint part is pulled can be maintained. By rotating the dial 32c in the opposite direction, the pulling of the joint part is released.

By imaging the space part of the finger pulled as described above, the edge of the cartilage C of the articular head Ah of the bone B1 can be imaged in the state as shown in FIG. 18 where the articular head Ah of the bone B1 (the thorax side (metacarpal) in this case) does not overlap with and is not shielded by the rim Br of the articular fossa Af of the bone B2 (the periphery side (proximal phalange) in this case) when viewed from the radiation generating device 11.

In this case, if the force to pull the joint part is too strong, the patient may feel pain. Hence, the fixing unit 20 is preferably configured not to pull a joint part with a force of larger than a predetermined amount.

More specifically, for example, the dial 32c may be provided with a torque limiter or the like, whereby when a radiologist turns the dial 32c too much by mistake and accordingly the amount of force to pull a joint part is larger than a predetermined amount, the dial 32c runs idle and accordingly the amount of force to pull the joint part does not become larger than the predetermined amount. This can surely prevent a patient from feeing pain due to the force to pull a joint part being too strong, and can perform safe imaging.

Although not shown, in addition to the dials 32a to 32c, a holding release button may be provided, and an operation on the holding release button at the end of imaging may return the operations performed with the dials 32a to 32c to a predetermined position(s) (e.g. the initial position(s) where tight fastening with the belt 30, angle adjustment and finger pulling are all released). This imaging release button may be provided for each of the dials 32a to 32c, or this one button may release all the operations.

In the above first configuration example, the dials 32a to 32c are for tight fastening with the belt 30, angle adjustment and finger pulling, respectively. They are thus arranged with consideration for a radiologist or the like to operate the dials in order, following the flow of the work to fix a finger of a patient to the fixing unit 20. Preferably, these operation members, namely, such as the dials 32a to 32c, are arranged suitable for operational flow. Therefore, in the above first configuration example, the dials 32a to 32c are for tight fastening with the belt 30, angle adjustment and finger pulling, respectively, from the top. In reverse, the dials 32c, 32b and 32a may be for tight fastening with the belt 30, angle adjustment and finger pulling, respectively, from the bottom.

Further, as with the angle of a finger in the up-down direction, the fixing unit 20 is preferably configured to measure the space between the thorax side and the periphery side of a joint part extended by pulling the joint part.

In this case too, in order that the fixing unit 20 is configured to measure the space between the thorax side and the periphery side of a joint part extended by pulling the joint part, for example, the dial 32c may be graduated in numerical values of space which increases in the rotational direction with 0 mm at the start point of the rotation of the dial 32c or provided with a display unit to display space which increases or decreases according to the amount of the rotation of the dial 32c, for example.

By measuring and recording the space when pulling the space part of a finger, the pulling amount of the space part can be easily and properly adjusted from the next imaging by making the pulling amount agree with the measured and recorded space.

Further, by making the pulling amount of a joint part fixed in all of the times that imaging is performed as described above, the distance between the articular head Ah of the bone B1 and the rim Br of the articular fossa Af of the bone B2 shown in FIG. 18 remains the same in all of the times that imaging is performed. Consequently, change over time (i.e. change over all of the times that imaging is performed) in the position of the edge of the cartilage C (i.e. thickness of the cartilage C) with respect to the articular head Af of the bone B1 or the rim Br of the articular fossa Af of the bone B2 is easily and accurately understandable.

Therefore, a doctor or the like who looks at a differential phase image can accurately recognize, for example, whether or not the thickness of the cartilage C decreases over time and accordingly carry out appropriate treatment or the like.

Second Configuration Example

Figure 24:
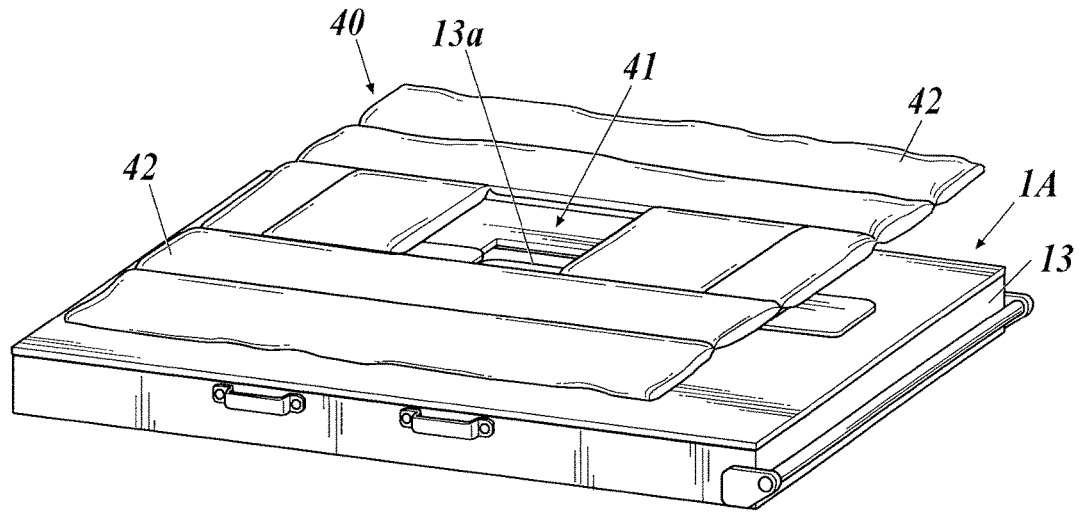
FIG. 24 is a perspective view showing a second configuration example of the fixing unit.

In a second configuration example of the fixing unit, a fixing unit 40 to perform position fixing and angle adjustment of a knee joint part in particular is explained. FIG. 24 is a perspective view showing the second configuration example of the fixing unit. The fixing unit 40 of the second configuration example has an opening 41 at the center, namely, is configured as a vacuum cushion.

More specifically, as shown in FIG. 24, the fixing unit 40 is formed of a plurality of bag-shaped members 42 which are each hollow and rectangular and combined to be the shape of a sheet having the opening 41 at the center. It is unnecessary for each bag-shaped member 42 and the fixing unit 40 to be rectangular.

The bag-shaped members 42 partly communicate with their adjacent bag-shaped members 42, whereby the air inside the bag-shaped members 42 can move into the adjacent bag-shaped members 42. Further, one of the bag-shaped members 42 (or two or more of the bag-shaped members 42) of the fixing unit 40 is provided with a not-shown hose to which a not-shown suction pump to suck the air in the bag-shaped members 42 is attached.

The air inside the bag-shaped members 42 is sucked by the suction pump-attached hose, whereby the air inside all the bag-shaped members 42 of the fixing unit 40 can be drawn out. As the suction pump, for example, a diaphragm pump which is easy to handle can be used.

Although not shown, in each bag-shaped member 42, a large number of microspheres formed of resin, such as spherical pieces of urethane foam, are contained. The microspheres in each bag-shaped member 42 cannot move to another bag-shaped member 42. Hereinafter, they are explained as microspheres, but do not need to be spherical and can be formed in any appropriate shape.

When imaging is performed, as shown in FIG. 24, the fixing unit 40 configured as described above is placed on the subject table 13 of the medical imaging device 1A. That is, the fixing unit 40 is placed on the subject table 13 such that the opening 41 of the fixing unit 40 is positioned over an opening part 13a (see FIG. 24 and FIG. 25 and FIG. 26 described below) provided on the optical path part of radiation in the subject table 13. The opening part 13a of the subject table 13 is an opening part meaning a part which is not shielded by lead or the like and transmits radiation. Hence, the opening part 13a may be closed by a radiation transmitting member.

On the fixing unit 40, a leg (i.e. the right leg or the left leg) of a patient on an imaging target side is placed. The leg of the patient is placed on the fixing unit 40 such that a knee joint part as an imaging target region is positioned over the opening 41 of the fixing unit 40. This allows the fixing unit 40 not to be present on the optical path of radiation which is emitted to and passes through the knee joint part of the patient downward.

Figure 25:
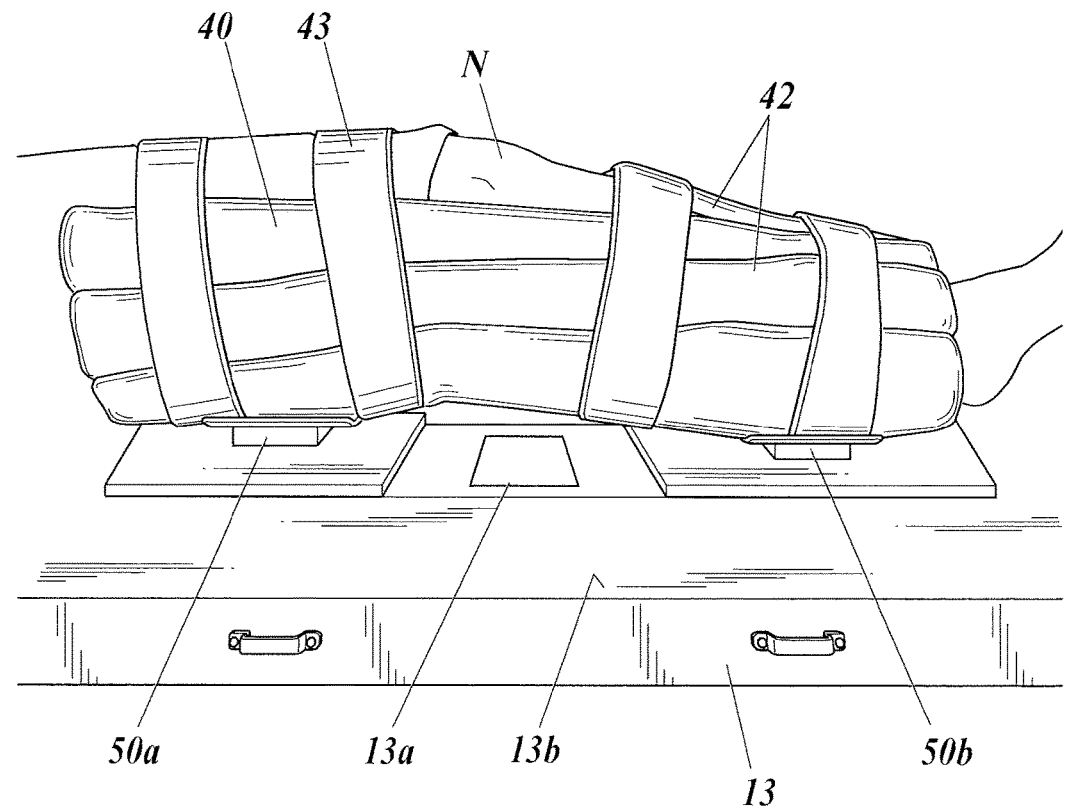
FIG. 25 is a perspective view showing the state or the like in which both ends of the fixing unit of the second configuration example are lifted such that the fixing unit fits a leg of a patient and the air inside bag-shaped members is removed.

Then, as shown in FIG. 25 for example, both ends of the fixing unit 40 are lifted such that the fixing unit 40 fits the leg of the patient. At the time, the angle of the knee N joint part of the patient is adjusted to a desired angle. (In FIG. 25, the angle is adjusted to an angle at which the knee N joint part is bent a little.) When the air inside the fixing unit 40 is sucked by the suction pump in this state, the air inside the bag-shaped members 42 is drawn out.

The large number of microspheres in each bag-shaped member 42 can freely move when the fixing unit 40 is moved with the air present in each bag-shaped member 42. Hence, for example, when both ends of the fixing unit 40 are lifted as described above, because the air is present in each bag-shaped member 42, the microspheres can move in each bag-shaped member 42, and accordingly the fixing unit 40 can be easily transformed into a state of fitting the leg of the patient.

However, once the air inside each bag-shaped member 42 is drawn out as described above, space in each bag-shaped member 42, the space where the microspheres can move, disappears, and accordingly the microspheres cannot move in each bag-shaped member 42, and the bag-shaped members 42 are made to be in a state of not easily being transformed. Thus, by configuring the fixing unit 40 as described above and drawing out the air in the bag-shaped members 42, the fixing unit 40 can be made to be in the state of not easily being transformed.

Therefore, when the fixing unit 40 configured as described above is used, by removing the air in the bag-shaped members 42 of the fixing unit 40 in the state of the fixing unit 40 fitting a leg of a patient, the joint part (i.e. the thorax side and the periphery side of the joint part) of the knee N as an imaging target can be fixed and held with the fixing unit 40 in a state in which the angle of the joint part is adjusted.

Further, as described above, by placing the fixing unit 40 on the subject table 13 such that the opening 41 of the fixing unit 40 is positioned over the opening part 13a of the subject table 13 of the medical imaging device 1A and removing the air in the bag-shaped members 42 for fixing in the state of the fixing unit 40 fitting a leg of a patient, the joint part (i.e. the thorax side and the periphery side of the joint part) of the knee N of the patient can be fixed with the fixing unit 40 with respect to the radiation emitted from the radiation generating device 11 (see FIG. 20).

Then, as shown in FIG. 25, by tightening a belt 43 for fixing from the outside of the fixing unit 40 in the state of the fixing unit 40 holding the leg of the patient as described above, the leg of the patient can be more properly fixed and held. The fixing unit 40 is, as shown in FIG. 25, preferably in a state of exposing the knee N joint part of the patient as the imaging target, not being present above the knee N joint part.

If the fixing unit 40 is not formed of a plurality of bag-shaped members 42 as described above, but is formed of one bag-shaped member (i.e. one bag-shaped member is the fixing unit), when both ends of the fixing unit 40 are lifted, the microspheres in the bag-shaped member move downward by gravity, so that the large number of microspheres are gathered on the lower side of the fixing unit 40 and no microspheres are present at the parts of the both ends which are lifted upward.

If the air inside the bag-shaped member is removed in such a state, the parts of the both ends lifted upward become in a state in which the films of the inside and the outside of the bag-shaped member stick to each other, and therefore the fixing unit 40 cannot be in the state of fixing and holding a leg of a patient as described above.

However, as described above, if the fixing unit 40 is formed of a plurality of bag-shaped members 42 combined and is configured not to allow the microspheres in each bag-shaped member 42 to move to another bag-shaped member 42, when both ends of the fixing unit 40 are lifted upward, the microspheres in each bag-shaped member 42 stay inside the bag-shaped member 42. That is, it does not cause the above-described situation where the microspheres are gathered on the lower side of the fixing unit 40 and no microspheres are present at the parts of the both ends.

Thus, by removing the air in the bag-shaped members 42 of the fixing unit 40 in the state of the fixing unit 40 fitting a leg of a patient, the joint part (i.e. the thorax side and the periphery side of the joint part) of the knee as an imaging target can be properly fixed and held with the fixing unit 40. As described above, in the second configuration example, a plurality of bag-shaped members 42 and a plurality of microspheres contained in each bag-shaped member 42 constitute a fixing jig of the fixing unit 40 to fix the thorax side and the periphery side of a joint part in the state in which the angle thereof is adjusted.

The fixing unit 40 of the second configuration example can fix and hold a leg of a patient in the state in which the angle of the knee joint part of the patient is adjusted to a desired angle as described above. However, this only may not place the knee joint part as shown in FIG. 18 where the articular head Ah of the bone B1 (the thorax side (femur) in this case) and the rim Br of the articular fossa Af of the bone B2 (the periphery side (tibia or fibula) in this case) do not overlap when viewed from the radiation generating device 11 (see FIG. 20).

Figure 26:
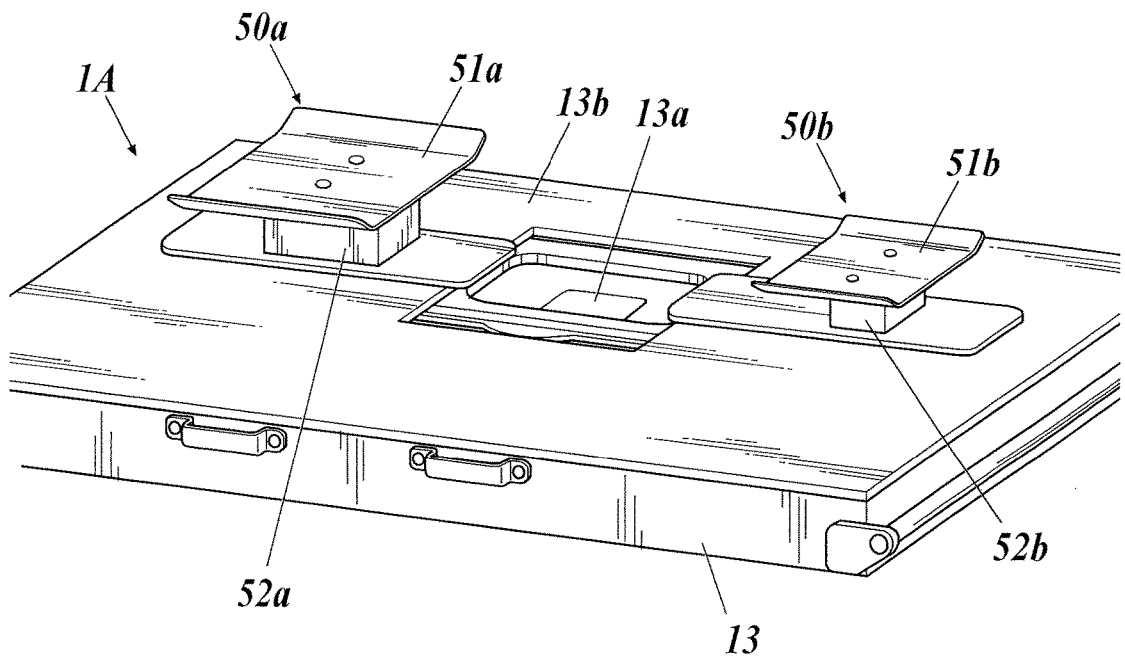
FIG. 26 is a perspective view showing lift mechanisms provided on a subject table.

Hence, when the fixing unit 40 of the second configuration example is used, as shown in FIG. 25 and FIG. 26 for example, the subject table 13 of the medical imaging device 1A is preferably provided with lift mechanisms 50a, 50b to change distances from the upper face 13b of the subject table 13 to the thorax side (femur) and the periphery side (tibia or fibula) of a joint part fixed by the fixing unit 40.

As shown in FIG. 26 for example, the lift mechanisms 50a, 50b can be configured to have placement tables 51a, 51b where the femoral region and the calf covered with the fixing unit 40 are placed, respectively, on their upper end parts, and also have support members 52a, 52b which support and lift/lower the placement tables 51a, 51b, respectively, under the placement tables 51a, 52b.

The placement tables 51a, 51b can be configured to be lifted and lowered by lifting and lowering the support members 52a, 52b with a not-shown elevator(s) provided on the subject table 13. In this case, the placement tables 51a, 51b are configured to be lifted and lowered independently from each other. Instead of both of the placement tables 51a, 51b to be configured to be lifted and lowered, it is possible that the distance to one placement table from the subject table 13 is fixed, and the other placement table is configured to be lifted and lowered.

This configuration changes at least one of the distance between the thorax side (femur) of a knee joint part and the subject table 13 and the distance between the periphery side (tibia or fibula) thereof and the subject table 13, whereby the fixing unit 40 (see FIG. 25, etc.) can adjust the angle formed of the thorax side (femur) and the periphery side (tibia or fibula) of the knee joint part with respect to the radiation emission direction, the angle being adjusted and fixed by the fixing jig (i.e. the fixing unit 40).

Consequently, a subject can be placed as shown in FIG. 18 where the articular head Ah of the bone B1 (the thorax side (femur) in this case) and the rim Br of the articular fossa Af of the bone B2 (the periphery side (tibia or fibula) in this case) do not overlap when viewed from the radiation generating device 11. Therefore, the edge of the cartilage C of the joint part can be well imaged in a differential phase image reconstructed from moire images taken by the medical imaging device 1A.

In the above, the fixing unit 40 of the second configuration example is used to image a knee joint part. However, the fixing unit 40 of the second configuration example can be used to image, for example, an ankle joint part, and also can be used to image a relatively large joint part of any of four limbs, such as a shoulder, elbow or hip joint.

Advantageous Effects

As described above, according to the medical imaging device 1A of the embodiment, the subject table 13 is provided with the fixing unit 20 or 40 which fixes the positions of the thorax side and the periphery side of a joint part as an imaging target region with respect to radiation emitted from the radiation generating device 11. The fixing unit 20 or 40 is configured to adjust the angle formed of the thorax side and the periphery side of the joint part.

Hence, by adjusting the angle formed of the thorax side and the periphery side of the joint part with the fixing unit 20 or 40, the subject is placed as shown in FIG. 18 where the articular head Ah of one bone B1 and the rim Br of the articular fossa Af of the other bone B2 do not overlap when viewed from the radiation generating device 11. Consequently, moire images can be taken in the state in which the articular head Ah of the bone B1 is not shielded by the rim Br of the articular fossa Af of the bone B2.

Then, by reconstructing a differential phase image based on thus-taken moire images, as shown in FIG. 9 and FIG. 18 for example, the edge (see A1 in FIG. 9) of the cartilage C of the articular head Ah of the bone B1 can be well imaged in the differential phase image.

Hence, a doctor or the like who looks at the differential phase image can accurately recognize, for example, whether or not the thickness of the cartilage C decreases over time and accordingly carry out appropriate treatment or the like.

Further, the thickness, shape or the like of the cartilage C imaged in the differential phase image can be accurately evaluated, and quantitative measurement of the thickness of the cartilage C or the like can be performed.

In the above embodiment, the thorax side (metacarpal or femur) of a joint part has the articular head Ah, and the periphery side (proximal phalange, fibula or tibia) thereof has the articular fossa Af. Needless to say, however, the present invention is applicable to the case where the periphery side of a joint part has the articular head Ah, and the thorax side thereof has the articular fossa Af.

Further, regarding the fixing unit 40 of the second configuration example in particular, as shown in FIG. 26 or the like, when the subject table 13 of the medical imaging device 1A is provided with the lift mechanisms 50a, 50b to change the distances from the upper face 13b of the subject table 13 to the thorax side (femur) and the periphery side (fibula or tibia) of a joint part fixed by the fixing unit 40, a leg of a patient including the knee joint part as a subject is lifted by the lift mechanisms 50a, 50b.

Thereby, the distance between the knee joint part of the patient as the subject and the subject table 13 is long, and accordingly the distance between the first grating 14 (G1 grating, see FIG. 20) provided immediately under the subject table 13 and the subject is long. Consequently, the level of image signals of moire images to be taken may be low.

Figure 27:
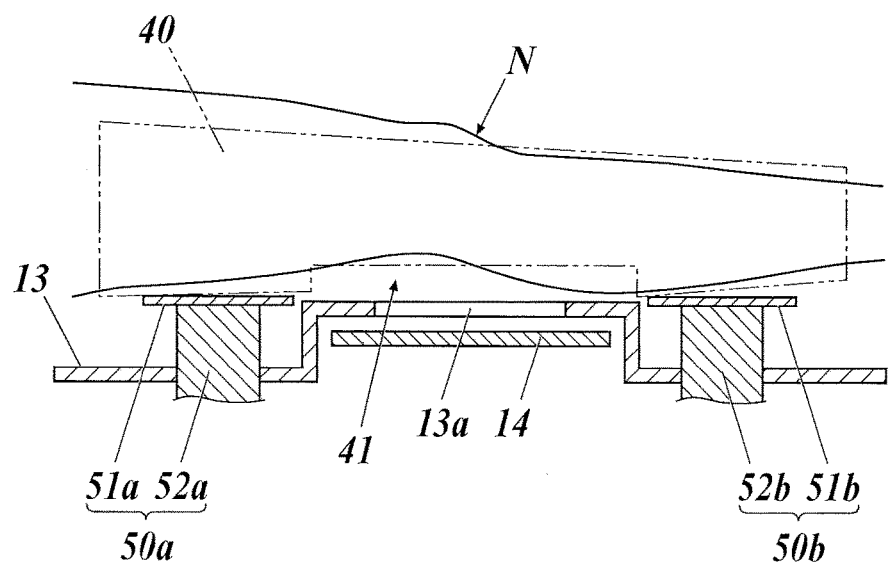
FIG. 27 shows a configuration example of the case where a part of the subject table is configured to be convex upward, the part including an opening part, and a first grating is arranged immediately under the convex part.

In order to reduce the possibility that such a problem arises, as shown in FIG. 27 for example, a part of the subject table 13 between the lift mechanisms 50a, 50b, the part including the opening part 13a, can be configured to be convex upward as compared with the other part of the subject table 13, and the first grating 14 can be arranged immediately under this convex part of the subject table 13, namely, inside the convex part.

This configuration can make the distance between a knee joint part of a patient as a subject and the first gating 14 shorter and accordingly make the first grating 14 closer to the knee joint part, and therefore can surely prevent the level of image signals of the subject of moire images to be taken from being low.

The medical imaging device 1A of the embodiment has been developed, as described above, to place a subject such that the articular head Ah of one bone B1 and the rim Br of the articular fossa Af of the other bone B2 do not overlap so as to image the edge of the cartilage C in a differential phase image.

However, the present invention is also applicable to the case where, for another purpose, the medical imaging device 1A with a Talbot interferometer or Talbot-Lau interferometer fixes the position of a joint part of a patient on the subject table 13, and takes moire images in the state in which the angle formed of the thorax side and the periphery side of the joint part is adjusted. This case is also included in the scope of claims of the present invention.

For example, the present invention is applicable to the case where the medical imaging device 1A images an injured region or a lesion site, such as a broken bone, of a non-cartilage part in a joint part of, for example, a finger, a knee, a shoulder, an elbow or a hip joint or in the vicinity thereof by fixing it with the fixing unit 20, 40 or the like of the first configuration example, the second configuration example or the like in a state in which the angle of the joint part remains the same in every imaging, and, for example, diagnosis is made about change of the injured region or the lesion site over time.

In this case, placement of a subject is not limited to the case where the subject is placed as described in the above embodiment in which the articular head Ah of one bone B1 and the rim Br of the articular fossa Af of the other bone B2 do not overlap, but includes the case where the joint part is fixed at an appropriate angle such as an angle at which the injured region or the lesion site becomes easy to see.

Needless to say, the present invention is not limited to the above embodiments, and can be appropriately modified as long as the modifications do not depart from the spirit of the present invention.

The entire disclosure of Japanese Patent Application No. 2013-157235 filed on Jul. 30, 2013 and Japanese Patent Application No. 2013-189957 filed on Sep. 13, 2013, including the specifications, claims, drawings and abstracts, is incorporated in this application by reference in their entirety.

INDUSTRIAL APPLICABILITY

Applicability is present in the field where radiological images are taken (the field of medical service, in particular).

DESCRIPTION OF REFERENCE NUMERALS

1 X-ray Imaging Device
11 X-ray Source
12 Multi-slit
12a Drive Unit
13 Subject Table
14 First Grating
15 Second Grating
16 X-ray Detector
17 Holding Unit
17a Buffer Member
18 Main Body Unit
181 Control Unit
182 Operation Unit
183 Display Unit
184 Communication Unit
185 Storage Unit
18a Drive Unit
5 Controller
51 Control Unit
52 Operation Unit
53 Display Unit
54 Communication Unit
55 Storage Unit
1A Medical Imaging Device
20, 40 Fixing Unit
42 Bag-shaped Member (Fixing Jig)
Af Articular Fossa
B1 Bone (Thorax Side)
B2 Bone (Periphery Side)
S Slit

The invention claimed is:
1. A medical image system comprising:
an X-ray imaging device comprising a Talbot interferometer or Talbot-Lau interferometer; and
a hardware processor configured to:
generate, among three reconstructed images of a differential phase image, an absorption image and a small-angle scattering image, at least the differential phase image based on an image signal obtained by the X-ray imaging device imaging a joint part;
extract a region of a joint cartilage based on the generated differential phase image;
analyze the extracted region of the joint cartilage so as to calculate a feature value indicating a state of the joint cartilage; and
compare the calculated feature value with a predetermined reference value and determine, based on a result of the comparison, into which one of predetermined scores of multiple stages the state of the joint cartilage falls.

2. The medical image system according to claim 1, wherein
the hardware processor is configured to calculate a length of a contour of the joint cartilage as the feature value, and
the hardware processor is configured to compare the length of the contour of the joint cartilage with the predetermined reference value and determine, based on the result of the comparison, into which one of the predetermined scores of the multiple stages the state of the joint cartilage falls.

3. The medical image system according to claim 1, wherein
the hardware processor is configured to calculate a thickness of the joint cartilage as the feature value, and
the hardware processor is configured to compare the thickness of the joint cartilage with the predetermined reference value and determine, based on the result of the comparison, into which one of the predetermined scores of the multiple stages the state of the joint cartilage falls.

4. The medical image system according to claim 1, wherein
the hardware processor is configured to calculate a difference value between a maximum value and a minimum value of thickness of the joint cartilage as the feature value, and
the hardware processor is configured to compare the difference value with the predetermined reference value and determine, based on the result of the comparison, into which one of the predetermined scores of the multiple stages the state of the joint cartilage falls.

5. The medical image system according to claim 1, wherein
the hardware processor is configured to calculate an area of the joint cartilage as the feature value, and
the hardware processor is configured to compare the area of the joint cartilage with the predetermined reference value and determine, based on the result of the comparison, into which one of the predetermined scores of the multiple stages the state of the joint cartilage falls.

6. The medical image system according to claim 1, wherein
the X-ray imaging device with the Talbot interferometer or Talbot-Lau interferometer includes:
a plurality of slit-formed gratings;
a subject table which holds a subject;
a radiation generating device which emits radiation so as to irradiate the subject; and
a radiation detector which is disposed on a downstream side of the subject table in a radiation emission direction and reads, as the image signal, an electric signal generated by two-dimensionally arranged conversion elements which generate the electric signal according to the emitted radiation,
in a state in which, as the subject, the joint part of a person is placed on the subject table, the radiation generating device emits the radiation, and the radiation detector takes a moire image with the radiation having passed through the joint part and the gratings,
the subject table is provided with a fixing unit which fixes positions of a thorax side and a periphery side of the joint part with respect to the radiation emitted from the radiation generating device, and the fixing unit is configured to adjust an angle formed of the thorax side and the periphery side of the joint part.

7. The medical image system according to claim 6, wherein the fixing unit is configured to adjust the angle formed of the thorax side and the periphery side of the joint part by adjusting an angle of a side having an articular fossa among the thorax side and the periphery side of the joint part.

8. The medical image system according to claim 6, wherein the fixing unit is configured to measure the adjusted angle.

9. The medical image system according to claim 6, wherein the fixing unit is further configured to pull the joint part in a direction to extend space between the thorax side and the periphery side.

10. The medical image system according to claim 9, wherein the fixing unit is configured not to pull the joint part with a force of larger than a predetermined amount.

11. The medical image system according to claim 9, wherein the fixing unit is configured to measure the pulled space.

12. The medical image system according to claim 6, wherein the fixing unit includes a fixing jig which fixes the thorax side and the periphery side of the joint part in a state in which the angle is adjusted.

13. The medical image system according to claim 12, wherein the fixing unit is configured to adjust the angle formed of the thorax side and the periphery side of the joint part with respect to the radiation emission direction, the angle being adjusted and fixed by the fixing jig, by at least one of a distance between the thorax side of the joint part and the subject table and a distance between the periphery side of the joint part and the subject table being changed.

14. The medical image system according to claim 13, wherein a part of the subject table which is on a downstream side of the subject in the radiation emission direction is formed to be convex in a direction to approach the subject, and a first grating among the gratings is disposed inside the convex part of the subject table.

15. A joint cartilage state score determination method comprising:

generating, among three reconstructed images of a differential phase image, an absorption image and a small-angle scattering image, at least the differential phase image based on an image signal obtained by an X-ray imaging device comprising a Talbot interferometer or Talbot-Lau interferometer imaging a joint part;

extracting a region of a joint cartilage based on the generated differential phase image;

analyzing the extracted region of the joint cartilage so as to calculate a feature value indicating a state of the joint cartilage; and comparing the calculated feature value with a predetermined reference value and determining, based on a result of the comparison, into which one of predetermined scores of multiple stages the state of the joint cartilage falls.

* * * * *